US010851132B2

(12) United States Patent
Yoon

(10) Patent No.: US 10,851,132 B2
(45) Date of Patent: *Dec. 1, 2020

(54) PROTEIN BASED ADHESIVE COMPOSITION AND METHOD

(71) Applicant: Won-Joon Yoon, Seoul (KR)

(72) Inventor: Won-Joon Yoon, Seoul (KR)

(73) Assignee: SEWON BIOTECHNOLOGY INC., Seoul (KR)

(*) Notice: Subject to any disclaimer, the term of this patent is extended or adjusted under 35 U.S.C. 154(b) by 29 days.

This patent is subject to a terminal disclaimer.

(21) Appl. No.: 15/903,956

(22) Filed: Feb. 23, 2018

(65) Prior Publication Data

US 2018/0282371 A1    Oct. 4, 2018

Related U.S. Application Data

(63) Continuation-in-part of application No. PCT/KR2016/009066, filed on Aug. 18, 2016.

(30) Foreign Application Priority Data

Aug. 26, 2015   (KR) .................. 10-2015-0120097

(51) Int. Cl.

| | | |
|---|---|---|
| *A61K 38/16* | (2006.01) | |
| *A61K 38/10* | (2006.01) | |
| *A61K 38/08* | (2019.01) | |
| *A61K 38/04* | (2006.01) | |
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 7/04* | (2006.01) | |
| *C09J 189/00* | (2006.01) | |
| *C07K 7/06* | (2006.01) | |
| *C07K 7/08* | (2006.01) | |
| *C07K 14/00* | (2006.01) | |
| *C07K 14/435* | (2006.01) | |
| *C09J 11/06* | (2006.01) | |
| *C09J 7/30* | (2018.01) | |
| *C07K 17/14* | (2006.01) | |

(52) U.S. Cl.
CPC ............. *C07K 7/04* (2013.01); *A61K 38/04* (2013.01); *A61K 38/08* (2013.01); *A61K 38/10* (2013.01); *A61K 38/16* (2013.01); *C07K 7/06* (2013.01); *C07K 7/08* (2013.01); *C07K 14/001* (2013.01); *C07K 14/43586* (2013.01); *C09J 7/30* (2018.01); *C09J 11/06* (2013.01); *C09J 189/00* (2013.01); *C07K 17/14* (2013.01); *C09J 2400/126* (2013.01); *C09J 2400/146* (2013.01); *C09J 2400/16* (2013.01); *C09J 2400/228* (2013.01); *C09J 2489/00* (2013.01)

(58) Field of Classification Search
None
See application file for complete search history.

(56) References Cited

U.S. PATENT DOCUMENTS

| | | | | |
|---|---|---|---|---|
| 5,018,847 | A | * | 5/1991 | Ojima ................... C12M 23/08 359/396 |
| 7,622,550 | B2 | | 11/2009 | Cha et al. |
| 8,845,851 | B2 | | 9/2014 | Allen et al. |
| 2010/0089287 | A1 | | 4/2010 | Thames et al. |
| 2016/0129044 | A1 | * | 5/2016 | Alio y Sanz ........ C12M 5/0653 424/422 |
| 2018/0085488 | A1 | * | 3/2018 | Yoon ...................... A61K 49/00 |

FOREIGN PATENT DOCUMENTS

WO    WO-2016153256 A1 *  9/2016 ............. A61K 49/00

OTHER PUBLICATIONS

Machine English language translation of WO 2016/153256 A1 published on Sep. 29, 2016, accessed on Espacenet at www.epo.org, 37 pages (Year: 2016).*
"Inert", The MSDS HyperGlossary, available online at http://www.ilpi.com/msds/ref/inert.html, 3 pages (2016) (Year: 2016).*
Vert et al., Pure Appl. Chem. 84:377-410 (2012) (Year: 2012).*
NCBI Database, Accession No. NP_001106733.1, 3 pages (last updated 2019) (Year: 2019).*
"N-terminal Acetylation and C-terminal Amidation," LifeTein, available online at https://www.lifetein.com/Peptide-Synthesis-Amidation-Acetylation.html, 4 pages (first available 2008) (Year: 2008).*
U.S. Appl. No. 16/328,476, filed Feb. 2019, Yoon, WJ.*
Filpula et al., "Structural and Functional Repetition in a Marine Mussel Adhesive Protein", Biotechnol. Prog., vol. 6, pp. 171-177, (1990).
Waite, "Nature's underwater adhesive specialist", Int. J. Adhesion and Adhesives, vol. 7, No. 1, pp. 9-14, (1987).
Yamamoto, "Marine Adhesive Proteins and Some Biotechnological Applications", Biotechnology and Genetic Engineering Reviews, vol. 13, No. 1, pp. 133-166, (1996).
Yu et al., "Synthetic Polypeptide Mimics of Marine Adhesives", Macromolecules, vol. 31, pp. 4739-4745, (1998).

* cited by examiner

*Primary Examiner* — Thea D'Ambrosio
(74) *Attorney, Agent, or Firm* — Vorys, Sater, Seymour & Pease LLP

(57) ABSTRACT

A protein adhesive of a novel sequence is disclosed. The protein adhesive according to the present disclosures enables adhesion between two non-biological materials or between a non-biological material and a biological material, thereby being applicable to various fields.

5 Claims, 19 Drawing Sheets

Specification includes a Sequence Listing.

Conjugation method 2: SS-bond conjugation,

PS, PC, Cellulose, Wood, Stainless, Metal

B, rhBMP2; CL, Cross-linker;
A7-1/B, cross-linked BMP2 and A7-1
C2C12, 48h

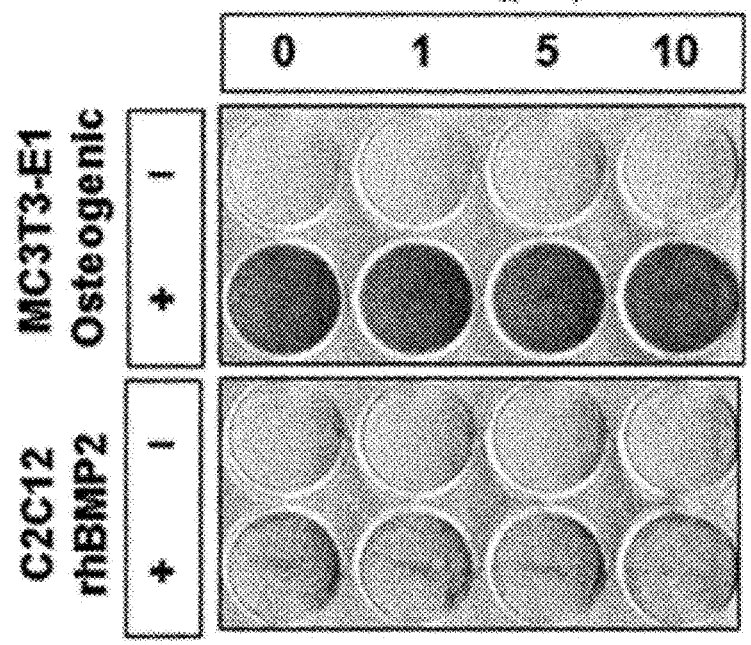

SEQUENCE LISTING

<160> NUMBER OF SEQ ID NOS: 71

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Gln Leu Val Val Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Gln Glu Glu Glu Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Gln Ala Ala Ala Lys
1               5

<210> SEQ ID NO 4
<211> LENGTH: 5
<212> TYPE: PRT
<213> ORGANISM: Artificial Sequence

```
<220> FEATURE:
<223> OTHER INFORMATION: Synthetic peptide

<400> SEQUENCE: 4

Asn Leu Val Val Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ser Leu Val Val Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Phe Arg Ala Leu Pro Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Phe Arg Glu Glu Pro Cys
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Phe Arg Val Val Pro Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Phe Glu Ala Leu Pro Cys
1               5

<210> SEQ ID NO 10
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 10

Tyr Arg Ala Leu Pro Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Trp Arg Ala Leu Pro Cys
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Phe Arg Ala Leu Pro
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Phe Arg Ala Leu
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Phe Arg Pro Cys
1

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Arg Gln Leu Val Val Lys
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
```

<400> SEQUENCE: 16

Phe Arg Ala Leu Pro Cys Arg Gln Leu Val Val Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide

<400> SEQUENCE: 17

Arg Gln Leu Val Val Lys Phe Arg Ala Leu Pro Cys
1               5                   10

<210> SEQ ID NO 18
<211> LENGTH: 24
<212> TYPE: PRT
<213> ORGANISM: Artificial Sequence
<220> FEATURE:
<223> OTHER INFORMATION: Synthetic peptide

<400> SEQUENCE: 18

Arg Gln Leu Val Val Lys Phe Arg Ala Leu Pro Cys Arg Gln Leu Val
1               5                   10                  15

Val Lys Phe Arg Ala Leu Pro Cys
            20

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Arg Gln Leu Val Val Lys Phe Arg Ala Leu Pro
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Arg Gln Leu Val Val Lys Phe Arg Ala Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Lys Gln Leu Val Val Lys Phe Arg Ala Leu Pro Cys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Arg Gln Lys Phe Arg Ala Leu Pro Cys
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Arg Gln Glu Glu Glu Lys Phe Arg Ala Leu Pro Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide

<400> SEQUENCE: 24

Arg Gln Ala Ala Ala Lys Phe Arg Ala Leu Pro Cys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Arg Gln Leu Val Val Lys Phe Arg Pro Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic peptide

<400> SEQUENCE: 26

Arg Gln Leu Val Val Lys Phe Arg Glu Glu Pro Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide

<400> SEQUENCE: 27

Arg Gln Leu Val Val Lys Phe Arg Val Val Pro Cys
1               5                   10

<210> SEQ ID NO 28
<211> LENGTH: 12
<212> TYPE: PRT
<213> ORGANISM: Artificial Sequence
<220> FEATURE:

```
<223> OTHER INFORMATION: Synthetic peptide

<400> SEQUENCE: 28

Arg Gln Glu Glu Glu Lys Phe Arg Glu Glu Pro Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide

<400> SEQUENCE: 29

Glu Gln Leu Val Val Glu Phe Glu Ala Leu Pro Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide

<400> SEQUENCE: 30

Arg Gln Leu Val Val Lys Tyr Arg Ala Leu Pro Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Arg Gln Leu Val Val Lys Trp Arg Ala Leu Pro Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

Arg Asn Leu Val Val Lys Phe Arg Ala Leu Pro Cys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

Arg Ser Leu Val Val Lys Phe Arg Ala Leu Pro Cys
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 34

Arg Gln Leu Val Val Gln Leu Val Val Lys Phe Arg Ala Leu Pro Cys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Arg Gln Leu Val Val Gln Leu Val Val Gln Leu Val Val Lys Phe Arg
1               5                   10                  15

Ala Leu Pro Cys
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic peptide

<400> SEQUENCE: 36

Arg Gln Leu Val Val Gln Leu Val Val Gln Leu Val Val Gln Leu Val
1               5                   10                  15

Val Lys Phe Arg Ala Leu Pro Cys
            20

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide

<400> SEQUENCE: 37

Arg Gln Leu Val Val Lys Phe Arg Ala Leu Pro Cys Phe Arg Ala Leu
1               5                   10                  15

Pro Cys

<210> SEQ ID NO 38
<211> LENGTH: 13
<212> TYPE: PRT
<213> ORGANISM: Artificial Sequence
<220> FEATURE:
<223> OTHER INFORMATION: Synthetic peptide

<400> SEQUENCE: 38

Arg Arg Gln Leu Val Val Lys Phe Arg Ala Leu Pro Cys
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide

<400> SEQUENCE: 39

Arg Arg Arg Arg Arg Gln Leu Val Val Lys Phe Arg Ala Leu Pro Cys
1               5                   10                  15
```

```
<210> SEQ ID NO 40
<211> LENGTH: 21
<212> TYPE: PRT
<213> ORGANISM: Artificial Sequence
<220> FEATURE:
<223> OTHER INFORMATION: Synthetic peptide

<400> SEQUENCE: 40

Arg Arg Arg Arg Arg Arg Arg Arg Arg Gln Leu Val Val Lys Phe
1               5                   10                  15

Arg Ala Leu Pro Cys
            20

<210> SEQ ID NO 41
<211> LENGTH: 26
<212> TYPE: PRT
<213> ORGANISM: Artificial Sequence
<220> FEATURE:
<223> OTHER INFORMATION: Synthetic peptide

<400> SEQUENCE: 41

Arg Arg Arg Arg Arg Arg Arg Arg Arg Arg Arg Arg Arg Arg Gln
1               5                   10                  15

Leu Val Val Lys Phe Arg Ala Leu Pro Cys
            20                  25

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide

<400> SEQUENCE: 42

Arg Gln Val Val Val Lys Phe Arg Ala Leu Pro Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Arg Gln Ile Val Val Lys Phe Arg Ala Leu Pro Cys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic peptide

<400> SEQUENCE: 44

Arg Gln Ala Val Val Lys Phe Arg Ala Leu Pro Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 45

Arg Gln Glu Val Val Lys Phe Arg Ala Leu Pro Cys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide

<400> SEQUENCE: 46

Arg Gln Leu Leu Val Lys Phe Arg Ala Leu Pro Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic peptide

<400> SEQUENCE: 47

Arg Gln Leu Ile Val Lys Phe Arg Ala Leu Pro Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic peptide

<400> SEQUENCE: 48

Arg Gln Leu Ala Val Lys Phe Arg Ala Leu Pro Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic peptide

<400> SEQUENCE: 49

Arg Gln Leu Glu Val Lys Phe Arg Ala Leu Pro Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic peptide

<400> SEQUENCE: 50

Arg Gln Leu Val Leu Lys Phe Arg Ala Leu Pro Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51
```

```
Arg Gln Leu Val Ile Lys Phe Arg Ala Leu Pro Cys
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Synthetic peptide

<400> SEQUENCE: 52

```
Arg Gln Leu Val Ala Lys Phe Arg Ala Leu Pro Cys
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Synthetic peptide

<400> SEQUENCE: 53

```
Arg Gln Leu Val Glu Lys Phe Arg Ala Leu Pro Cys
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

```
Arg Gln Leu Val Val Arg Phe Arg Ala Leu Pro Cys
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide

<400> SEQUENCE: 55

```
Arg Gln Leu Val Val Lys Phe Lys Ala Leu Pro Cys
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Synthetic peptide

<400> SEQUENCE: 56

```
Arg Gln Leu Val Val Glu Phe Glu Ala Leu Pro Cys
1               5                   10
```

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

Arg Gln Leu Val Val Lys Phe Arg Leu Leu Pro Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic peptide

<400> SEQUENCE: 58

Arg Gln Leu Val Val Lys Phe Arg Ile Leu Pro Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic peptide

<400> SEQUENCE: 59

Arg Gln Leu Val Val Lys Phe Arg Val Leu Pro Cys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide

<400> SEQUENCE: 60

Arg Gln Leu Val Val Lys Phe Arg Glu Leu Pro Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide

<400> SEQUENCE: 61

Arg Gln Leu Val Val Lys Phe Arg Ala Ala Pro Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide

<400> SEQUENCE: 62

Arg Gln Leu Val Val Lys Phe Arg Ala Ile Pro Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide

<400> SEQUENCE: 63

Arg Gln Leu Val Val Lys Phe Arg Ala Val Pro Cys

```
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: Synthetic peptide

<400> SEQUENCE: 64

Arg Gln Leu Val Val Lys Phe Arg Ala Glu Pro Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic peptide

<400> SEQUENCE: 65

Arg Gln Glu Glu Glu Glu Phe Glu Glu Glu Pro Cys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (11)
<223> OTHER INFORMATION: any amino acids

<400> SEQUENCE: 66

Arg Gln Leu Val Val Lys Phe Arg Ala Leu Xaa Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic peptide

<400> SEQUENCE: 67

Arg Gln Leu Val Val Lys Phe Arg Ala Leu Pro Ser
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic peptide

<400> SEQUENCE: 68

Arg Gln Leu Val Val Lys Phe Arg Ala Leu Pro Thr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic peptide
<220> FEATURE:

```
<221> NAME/KEY: VARIANT
<222> LOCATION: (12)
<223> OTHER INFORMATION: any amino acids

<400> SEQUENCE: 69

Arg Gln Leu Val Val Lys Phe Arg Ala Leu Pro Xaa
1               5                   10

<210> SEQ ID NO 70
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: variant
<222> LOCATION: (6)...(12)
<223> OTHER INFORMATION: n = a, g, c or t

<400> SEQUENCE: 70
carytngtng tnaar                                                      15

<210> SEQ ID NO 71
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(33)
<223> OTHER INFORMATION: n = a, g, c or t

<400> SEQUENCE: 71
mngcarytng tngtnaartt ymnggcnytn ccntgy                               36
```

PROTEIN BASED ADHESIVE COMPOSITION AND METHOD

CROSS-REFERENCE TO RELATED APPLICATIONS

The present application is a continuation in part application of International Patent Application PCT/KR2016/009066, filed Aug. 18, 2016, which claims the benefit of Korean Patent Application No. 2015-0120097, filed Aug. 26, 2015 in the Korean Intellectual Property Office, the disclosure of which are incorporated herein.

STATEMENT OF SEQUENCING LISTING

The Sequence Listing submitted in text format (.txt) filed on Apr. 10, 2020, named "SequenceListing.txt", created on Apr. 10, 2020 (15.7 KB), is incorporated herein by reference.

BACKGROUND OF THE INVENTION

Field of the Invention

The present disclosure relates to the polypeptide based adhesive composition having adhesive properties to various materials of biological or non-biological origin.

Description of the Related Art

Adhesion of plurality of materials to each other having the same or different properties, particularly having different structures or surface is an important process required in various field. However the problem that occurs in the adhesion process is that the nature of the problem differs depending on the type of the substance to be attached.

Particularly problematic areas are medical/biological fields, which require the adhesion of micro or nano-sized materials. Adhesion in the medical field can include the use in the suture of incised or damaged area, in the treatment of fractures of a bone, in the adhesion of the cornea, and the like, and can be used in the field of dentistry for treating tooth decay, sealant and gum surgery.

In such an environment, it is advantageous for the adhesive to be able to be adhered in a wet condition with moisture or water, and it is advantageous that the amount of adhesive used is minimized because small-sized components are usually involved. In addition, adhesives used in medical or biological fields must be safe for the use in cells, tissues or organisms and also have biocompatibility and further biodegradability so that they do not cause an inflammatory or toxic reaction.

However, most of the adhesives sold on the market are based on compounds that can be harmful to the environment and the human body. Therefore, a safe bio-based adhesive that is not harmful to the environment is needed to replace the current ones.

A representative bio-based adhesive is an adhesive using mefp1, Mytilus, Marine mussels protein (Waite, J H Int. J. Adhes. Adhes., 1987. 7 (1): 9-14; Yamamoto, H., Biotechnology and Genetic Engineering Reviews, 1996. 13: p. 133-65; and U.S. Pat. No. 7,622,550, Biotechnology and Genetic Engineering Reviews, 1996. 13: p. 133-65, and U.S. Pat. No. 7,622,550). These adhesives are known to be involved in DOPA (3,4-dihydroxyphenylalanine)-DOPA crosslinking (Deming, T. J., Polymeric Materials: Science and Engineering, 1999. 80: p. 471-472).

In addition, materials mimicking mussel protein based adhesives have also been developed. For example, it includes mussel protein based adhesives with improved adhesiveness produced by DNA recombinant technology and water soluble polypeptides containing DOPA and lysine (Filpula, D R, et al., Biotechnol. Prog., 1990. 6 (3): p. 171-7; and Yu, M. and T J Deming, Macromolecules, 1998. 31 (15): 4739-45).

In addition, U.S. Pat. No. 8,845,851 and US 2010-0089287 disclose protein binding compositions using soy protein.

However, there is a need to develop new protein-based adhesive or adhesive compositions with improved adhesiveness that can be applied in a variety of environments.

SUMMARY OF THE INVENTION

The present disclosure is to provide an adhesive composition for attaching various materials to various surfaces of organic and inorganic origins, the composition comprising novel polypeptides with improved adhesiveness with less or no toxicity having wide applications under various conditions and use thereof.

In one aspect, the present disclosure provides a composition comprising an isolated polypeptide having an amino acid sequence consisting of the amino acid sequence as set forth in SEQ ID NO: 17, 1, 6, 15, 16, 18-22, 24-27, 29-37, 42-64, 67 or 68.

In the previous compositions, the first amino acid of SEQ ID NO: 15-20, 22, 24-27, 30-37, 42-64, 67 and 68 is substituted with a lysine residue, the first amino acid of SEQ ID NO: 21 is substituted with an arginine, and the first amino acid of SEQ ID NO: 29 is substituted with an aspartic acid.

In the previous compositions, the first amino acid of SEQ ID NO: 15-22, 24-27, 30-37, 42-64, 67 and 68 is substituted with an aspartic acid or a glutamic acid residue, and the first amino acid of SEQ ID NO: 29 is substituted with a lysine or arginine residue.

In the previous compositions, the amino acid sequence of SEQ ID NO: 15-20, 22, 24-27, 30-37, 42-64, 67 or 68 further comprise up to 14 arginine residues at the N-terminus, the amino acid sequence of SEQ ID NO: 21 further comprises up to 14 lysine residues at the N-terminus, and the amino acid sequence of SEQ ID NO: 29 further comprises up to 14 glutamic acid residues.

In the previous compositions, wherein the N- or C-terminal of the polypeptide is modified by an inert group.

In the previous compositions, the composition is for attachment to an inorganic surface.

In the previous compositions, the inorganic surface is the surface of a metal, a ceramic, a calcium apatite crystal, or a polymer synthetic resin.

In the previous compositions, the materials attached to the surface are a biological or a non-biological material.

In the previous compositions, the non-biological material is a metal, a glass, a plastic, or a polymer synthetic resin, and the biological material is a cell, a tissue, a protein, a lipid, a sugar or a nucleic acid, or a combination thereof.

In the previous compositions, further comprising at least one of a surfactant, an oxidizing agent or a filler.

In the previous compositions, the filler is a collagen, a hyaluronic acid, a chondroitin sulfate, an elastin, a laminin, casein, a hydroxyapatite, an albumin, or a fibronectin.

In other aspect, the present disclosure provides a method of attaching at least two materials comprising the steps of: treating all or in part of the at least one of two material with the present composition as described above; contacting the at least two materials in a condition suitable for the attachment.

The order of the steps may be changed.

Thus, in other aspect, the present disclosure provides a method of attaching at least two materials comprising the steps of: contacting the at least two materials in a condition suitable for the attachment and treating all or in part of the at least one of two materials with the present composition as described above.

In the previous methods, the at least one material is an inorganic surface.

In the previous methods, the inorganic surface is the surface of a metal, a ceramic, a calcium apatite crystal, or a polymer synthetic resin.

In the previous methods, the at least one materials attached to the inorganic surface is a biological or a non-biological material.

In the previous methods, the non-biological material is a metal, a glass, a plastic, or a polymer synthetic resin, and the biological material is a cell, a tissue, a protein, a lipid, a sugar or a nucleic acid, or a combination thereof.

In other aspect, the present disclosure provides a method of preparing the composition described above comprising the step of providing a vector having a nucleic acid encoding the isolated polypeptide and expressing the vector in an appropriate cell.

In the previous method, the method may further comprise a step of isolating the polypeptide expressed in the cell.

Advantageous Effects

The present method and composition comprising the novel peptides of the present disclosure can be advantageously used as a bio-adhesive for attaching biological materials such as cells or tissues to various surfaces, particularly inorganic surfaces or used as a coating agent to coat the various surfaces, particularly inorganic surfaces.

The present adhesive composition and method are applied in a wet condition and are safe to use in cells not being toxic and inducing inflammations and thus have biocompatibility.

BRIEF DESCRIPTION OF THE DRAWINGS

In FIG. 1A, the peptides according one embodiment of the present disclosure conjugated to biotin via a disulfide bond were attached to a glass and the signal from the biotin was analyzed. The signal indicates that the present peptides are attached to the glass. The signal was disappeared when it was treated with DTT to remove disulfide bond indicating that the signals were from the biotin conjugated to the present peptides.

FIG. 1B is a schematical representation of the method employed in FIG. 1A, showing that the present peptides attached to the glass are conjugated to a biotin, which is then detected by an antibody to the biotin. The signal is disappeared by treatment with DTT that removes the SH bond and thus releases the biotin from the present peptides.

FIG. 1C is a schematical representation of the method to test the adhesiveness of the present peptide to various non-biological materials, which are basically identical to FIG. 1A except that FITC (fluorescein isothiocyanate) is used instead of biotin as a labeling agent.

FIG. 1D is the results of the analysis performed as described in FIG. 1C and shows the adhesiveness of the present peptides to various surfaces of non-biological materials. From left to right, the circles on each of the panel indicate PBS (phosphate buffer saline) only, FITC-conjugated A7-1, and FITC dye only, respectively.

FIG. 4A is the results showing that increasing adhesiveness of the cells by A7-1 does not require the treatment of the cells with electrolytes (EDTA treatment) and also do not require new protein synthesis (CHX treatment). However the adhesiveness was inhibited at an early stage by treatment of the cell with serum. This may be explained that various types of GAGs abundantly present in the serum firstly or preferentially bind to the present peptides, leaving less amount to the cells.

FIG. 4B is the results of testing the involvement of GAG or collagen in the mechanism of promoting the adhesiveness by the present peptides. The results show that both GAG and collagen are involved in the mechanism of promoting cell adhesiveness by the present peptides, evidenced by the results that the adhesiveness was disappeared when the cells were treated with enzymes to remove the potential targets. The decrease in the cell adhesiveness by treating cells with collagenase indicates that the increase in the adhesiveness is partly due to the interaction with the collagen. And the results from treatment with hyaluronidase indicate that the hydrolysis of heparin sulfate, thus the interaction between heparin sulfate in GAG and the present peptides, is also at least partly responsible for promoting the adhesiveness by the present peptides. A graph in the lower part is the results testing the involvement of GAG and shows that the adhesiveness increased by the present peptide A7-1 is significantly decreased in a concentration dependent manner by the addition of heparin and C-sulfate (CS). This indicates that GAGS are involved in the adhesiveness by the present peptide A7-1. The changes in the concentration of GAG are known to be related to the development of various diseases. Thus the present peptide may be utilized to control GAG concentration in blood or as drug carrier targeting GAG.

FIG. 4C is the results to test the present peptide adhesiveness in the presence of soluble RGDs peptides as a competitor and shows that in the absence of A7-1, the addition of RGDs significantly reduces the adhesiveness of the cells to the bottom because RGDs firstly or preferentially binds to adhesive molecule integrins. However, in the presence of A7-1, it is found that the cell adhesiveness is not affected by the addition of RGDs. This indicates that the present peptides have a distinct mechanism different from that of an anchorage dependent adhesiveness via integrin.

FIGS. 8A, 8B, and 8C are the results of testing the stability of the present peptides in osteoblast MC3T3-E1.

FIG. 10A is the results showing that numerous actin-rings, a sign that the cells are in an early stage of adhesiveness, were observed in negative control cells in contrast to the cells treated with the present peptide in which numerous stress fiber formations were observed indicating that the cells are in an advanced stage of adhesiveness.

FIG. 10B is a graph quantifying the results of FIG. 10A.

FIG. 10C is the results of measuring the geometric shape of the cells (cell aspect ratio: cells longitudinal/horizontal ratio, in which the value of the cells in a perfect round shape at an very early stage during the process of adhesiveness is near 1, and is increasing as the cells are attaching to the plate). The results show that the cells treated with the present peptide have an excellent adhesiveness compared to the control.

DETAILED DESCRIPTION OF THE EMBODIMENTS

Definitions

Figure 1A:
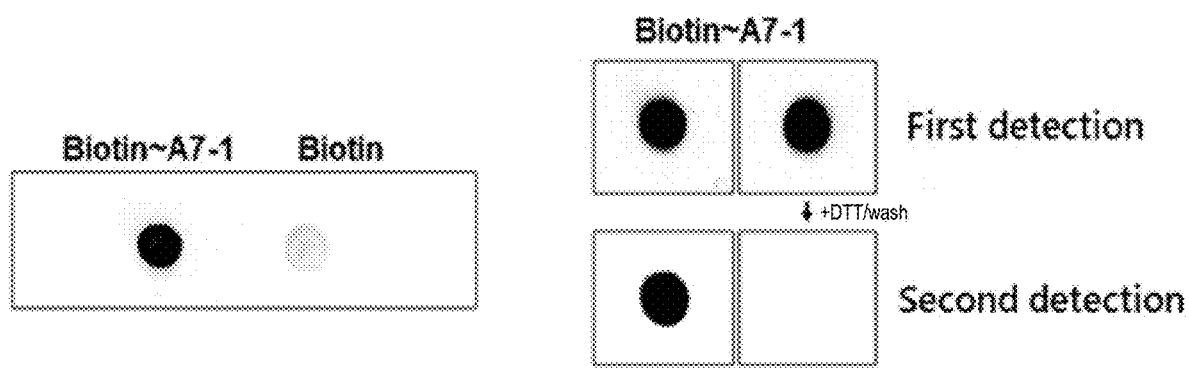
FIGS. 1A to 1D are results showing the adhesiveness of the peptide (A7-1) according to one embodiment of the present disclosure to glass, Zr, Vinyl, Polystyrene fiber, Polycaprolactone, Ti and Collagen (Col) as non-biological materials.
Figure 1B:
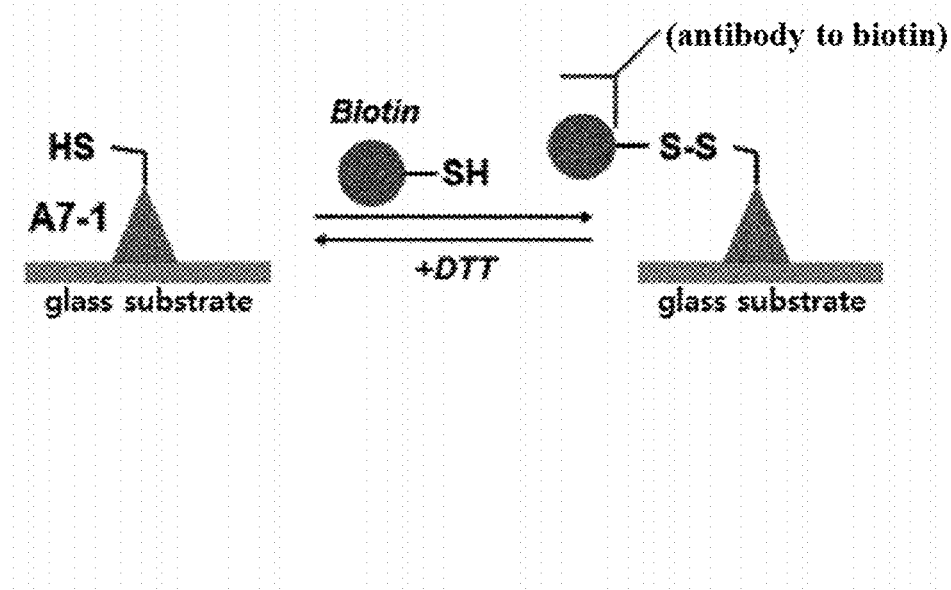
Figure 1C:
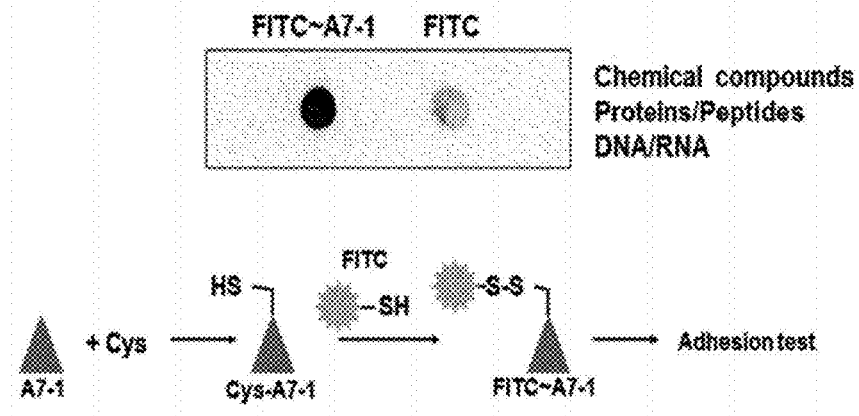
Figure 1D:
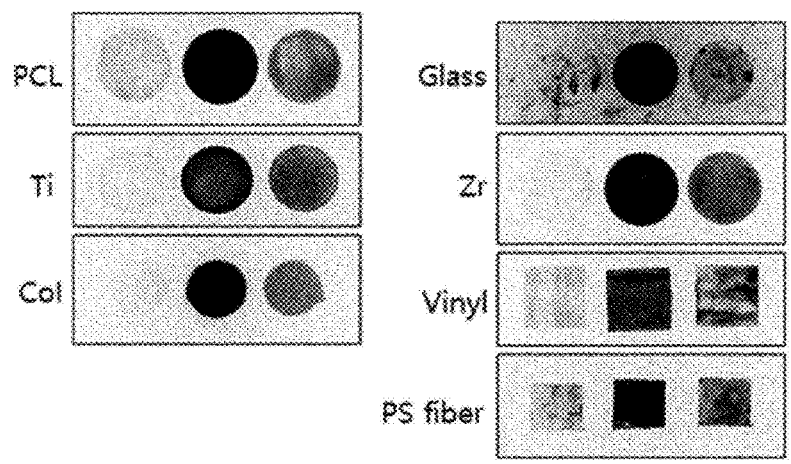

In the present disclosure, amino acids are denoted by single letter code as defined in the related art as follows: A, Alanine; R, Arginine; N, Asparagine; D, Aspartic acid; C, Cysteine; E, Glutamic acid; Q, Glutamine; G, Glycine; H, Histidine; I, Isoleucine; L, Leucine; K, Lysine; M, Methionine; F, Phenylalanine; P, Proline; S, Serine; T, Threonine; W, Tryptophan; Y, Tyrosine; V, Valine; Z, Glutamic acid and Glutamine; X, any amino acid.

As used herein the term "amino acid" refers to naturally occurring 20 amino acids or non-natural amino acids, as well as post-translationally modified amino acids, amino acid analogs and amino acid mimetics that function in a manner similar to the naturally occurring amino acids, including for example, phosphoserine and phosphothreonine; rare amino acids such as 2-aminoadipic acid, hydroxylysine, norvaline and norleucine; amino acids modified to improve their stability in cell and cell penetration; and optical isomers of D- and L-form. Positively charged amino acids, negatively charged amino acids, polar non-charged amino acids, and non-polar aliphatic amino acids, which may be used in the present disclosure, are well known in the art and may be selected by one of ordinary person in the art without difficulty.

As used herein, the terms "natural and non-natural" each refers to the compounds found in cells, tissues or bodies, and the compounds artificially modified thereto for a particular purpose, respectively.

As used herein, the term "peptides" and "polypeptides" are interchangeably used, and are read from N- to C-term unless defined otherwise and refer to a molecule in which amino acid monomers are covalently linked to each other, and are interpreted to include peptides comprised of native amino acids or their lysed products, synthetic peptides, peptides prepared in a recombinant manner, peptide mimetics (typically synthetic peptide), analogous such as peptoid and sempeptoids, and peptides modified to improve/change their function such as stability in cells. Examples of the modification include a N-term modification, a C-term modification, a peptide bond modification such as $CH_2$—NH, $CH_2$—S, $CH_2$—S=O and $CH_2$—$CH_2$, a back-bone modification, and side-chain modification. Peptide mimetics are prepared by methods known in the art, which may be referred to, for example, Quantitative Drug Design, C. A. Ramsden Gd., Choplin Pergamon Press (1992).

As used herein the term "adhesion" includes attachment or adsorption, including reversible or irreversible adhesion. In other aspects, the adhesion includes attachment or adsorption through at least one of chemical interactions including covalent bonds, ionic bonds, van der waals bonds, and hydrogen bonds.

In the present disclosure, inorganic materials or the surface of inorganic materials are used interchangeably. Inorganic materials include materials within the generally accepted meaning which do not contain carbon, silicon or nitrogen, or have a relatively free electron configuration due to high degree of electrostatic conductivity. Particularly included in the present disclosure are inorganic materials having a hydrophobic surface such as metal for example iron, copper, or noble metal including gold, silver or platinum, titanium, or aluminum; ceramics such as zirconia; calcium apatite crystals such as hydroxyl apatite; high molecular weight synthetic resins such as polyethylene and; glass and combinations thereof without being limited thereto.

The term "surface" as used herein is interpreted in the broadest sense and to be present in the materials having at least 2 dimensional structures without being limited to materials having particular shape and/or sizes. Also the surface at the molecular or unit level, and the surfaces formed by the materials comprised of such molecules or units are included. For example the surfaces included in the present disclosure can be found/present in particles in sizes ranging from few nanometer to few micrometer or materials in sizes ranging from few millimeters to few meters.

The Present Peptides

The present disclosure is based on the discovery that the present peptides as disclosed herein are able to various biological and non-biological materials to the surface of inorganic or organic materials.

Thus in one aspect, the present disclosure relates to a peptide or polypeptides or derivatives thereof or the composition comprising the same for attachments or for coating the surfaces for attachment as descried herein.

In one embodiment, the peptide having Formula I: $[X^1—X^2—X^3—X^4—X^5]_n$:
in which
$X^1$ is any amino acid,
$X^2$, $X^3$ and $X^4$, which may be identical or different, are each L, V, I, E or A, and
$X^5$ is K or R,
n is an integer from 1 to 5, if n is 2 or more, each polypeptide may be identical or different, wherein the amino acid is a natural or non-natural D- or L-form residue.

In the present disclosure, the peptide of formula I, also referred as a first domain/region, is found to be involved in the adhesion to cell surfaces or cell membranes and also can be present in multiple numbers depending on the particular applications of interest as described herein. Further the first region is considered a core region which may affect the secondary structure of the present peptides and assists in maintaining the molecular characteristics of the other regions as described below. Particularly the first region is hydrophobic in nature enabling hydrophobic interactions with molecules or cells of interest, and can be used advantageously for tissue regeneration for example being provided as nanostructured supports or a component of gels.

In the present disclosure, one or more of the first region or the peptide of formula I may be comprised in the present peptides and when more than one is present, each one may be identical or different. The number of formula I which may be included in the present peptides may be various and determined in consideration of the functionalization of interest of the present peptide such as for use in the preparation, storage or delivery, or in consideration of the effects or various applications as described hereinafter. For example, in formula I, n may be 1 to 10, 1 to 9, 1 to 7, 1 to 6, 1 to 5, 1 to 4, 1 to 3, 1 to 2, or 1.

In one embodiment of formula I, $X^1$ is any amino acids, particularly polar non-charged amino acids, more particularly S, T, C, P, N or Q.

In other embodiment of formula I, $X^2$, $X^3$ and $X^4$, which may be identical or different, and each are L, V, I, E or A. The sequence of $X^2$—$X^3$—$X^4$ are for example AAA, EEE, LVA, LVL, LVV, LLA, LLL, or LLV and the like without being limited thereto. In other embodiment, the formula I may be $X^1$-LVV-$X^5$, $X^1$-AAA-$X^5$ or $X^1$-EEE-$X^5$.

In one embodiment, the sequence of formula I is represented by QLVVK (SEQ ID NO: 1), QEEEK (SEQ ID NO: 2), QAAAK (SEQ ID NO: 3), NLVVK (SEQ ID NO: 4) or SLVVK (SEQ ID NO: 5).

In other aspect, the present disclosure relates to a peptide of formula II or a peptide of formula I further comprising formula II: [$X^6$—$X^7$—$X^8$—$X^9$—$X^{10}$—$X^{11}$]n, in formula II,
$X^6$ is any one of F, Y and W,
$X^7$ is K or R,
$X^8$ is any one of A, M and I
$X^9$ is any one of L, M and G,
$X^{10}$ is any amino acid, and
$X^{11}$ is any one of C, S and T,
wherein at least one group of ($X^7$ and $X^8$) and ($X^{10}$ and $X^{11}$) may be absent,
wherein n is 1 or 2.

In one embodiment, the peptide of formula II may be linked to an amino terminal (N-term) or a carboxy terminal (C-term), or both of N- and C-term of formula I.

According to the present disclosure, the peptide of formula II, referred to as a second region/domain, imparts a hydrophilic property to the present peptides facilitating the dissociation and may form an alpha helix as a secondary structure in combination with the peptide of formula I, when it is present as a single molecule.

In one embodiment, at least one of the peptide of formula I and formula II each may be included in the present peptide in various arrangements. For example, the present peptides may include a peptide in which at least one of peptide of formula I being connected to at least one of peptide of formula II, including for example a peptide of formula I-II, a peptide of formula II-I, a peptide of formula I-I-formula II-II, or in which at least two of consecutively connected peptides of formula I and II are further linked, including for example a peptide of formula or formula or formula The order may be changed.

In one embodiment of the present disclosure, the peptide of formula II is represented by FRALPC (SEQ ID NO: 6), FREEPC (SEQ ID NO: 7), FRVVPC (SEQ ID NO: 8), FEALPC (SEQ ID NO: 9), YRALPC (SEQ ID NO: 10), WRALPC (SEQ ID NO: 11), FRALP (SEQ ID NO: 12), FRAL (SEQ ID NO: 13), or FRPC (SEQ ID NO: 14).

In other aspect of the present disclosure, the peptide of formula I, II or the peptide including both formula I and II may further comprise a peptide of formula III called a third region: $X^{12}_{1-15}$ at its N- or C-term, including such as formula wherein $X^{12}$ is positively or negatively charged amino acids.

It is found in the present disclosure that charged amino acid(s) are required for formula III, particularly when present at N-term for proper function of the present peptides.

In one embodiment, in formula III, the positively charged amino acid is K or R.

In other embodiment, in formula III, the negatively charged amino acid is D or E.

In one embodiment, the present peptide may comprise the peptide of formula III up to 15.

In one embodiment of the present disclosure, the present peptides encompassed by formula I, formula II, or formula I and II, or formula I, formula II or formula I and formula II in combination with formula III that is linked at the N-term may be represented by: QLVVK (SEQ ID NO: 1), FRALPC (SEQ ID NO: 6), RQLVVK (SEQ ID NO: 15); FRALPCRQLVVK (SEQ ID NO: 16); RQLVVKFRALPC (SEQ ID NO: 17); RQLVVKFRALPCRQLVVKFRALPC (SEQ ID NO: 18); RQLVVKFRALP (SEQ ID NO: 19); RQLVVKFRAL (SEQ ID NO: 20); KQLVVKFRALPC (SEQ ID NO: 21); RQKFRALPC (SEQ ID NO: 22); RQEEEKFRALPC (SEQ ID NO: 23); RQAAAKFRALPC (SEQ ID NO: 24); RQLVVKFRPC (SEQ ID NO: 25); RQLVVKFREEPC (SEQ ID NO: 26); RQLVVKFRVVPC (SEQ ID NO: 27); RQEEEKFREEPC (SEQ ID NO: 28); EQLVVEFEALPC (SEQ ID NO: 29); RQLVVKYRALPC (SEQ ID NO: 30); RQLVVKWRALPC (SEQ ID NO: 31); RNLVVKFRALPC (SEQ ID NO: 32); RSLVVKFRALPC (SEQ ID NO: 33); R-(QLVV)$_2$—KFRALPC (SEQ ID NO: 34); R-(QLVV)$_3$—KFRALPC (SEQ ID NO: 35); R-(QLVV)$_4$-KFRALPC (SEQ ID NO: 36); RQLVVK-(FRALPC)$_2$ (SEQ ID NO: 37); (R)$_2$-QLVVKFRALPC (SEQ ID NO: 38); (R)$_5$-QLVVKFRALPC (SEQ ID NO: 39); (R)$_{10}$-QLVVKFRALPC (SEQ ID NO: 40); or (R)$_{15}$-QLVVKFRALPC (SEQ ID NO: 41).

In other embodiment of the present disclosure, the present peptides encompassed by formula I and II in combination with formula III at the N-term may be represented by: RQLVVKFRALPC (SEQ ID NO: 17); KQLVVKFRALPC (SEQ ID NO: 21); RNLVVKFRALPC (SEQ ID NO: 32); RSLVVKFRALPC (SEQ ID NO: 33); RQVVVKFRALPC (SEQ ID NO: 42); RQIVVKFRALPC (SEQ ID NO: 43); RQAVVKFRALPC (SEQ ID NO: 44); RQEVVKFRALPC (SEQ ID NO: 45); RQLLVKFRALPC (SEQ ID NO: 46); RQLIVKFRALPC (SEQ ID NO: 47); RQLAVKFRALPC (SEQ ID NO: 48); RQLEVKFRALPC (SEQ ID NO: 49); RQLVLKFRALPC (SEQ ID NO: 50); RQLVIKFRALPC (SEQ ID NO: 51); RQLVAKFRALPC (SEQ ID NO: 52); RQLVEKFRALPC (SEQ ID NO: 53); RQAAAKFRALPC (SEQ ID NO: 24); RQEEEKFRALPC (SEQ ID NO: 23); RQLVVRFRALPC (SEQ ID NO: 54); RQLVVKYRALPC (SEQ ID NO: 30); RQLVVKWRALPC (SEQ ID NO: 31); RQLVVKFKALPC (SEQ ID NO: 55); RQLVVEFEALPC (SEQ ID NO: 56); RQLVVKFRLLPC (SEQ ID NO: 57); RQLVVKFRILPC (SEQ ID NO: 58); RQLVVKFRVLPC (SEQ ID NO: 59); RQLVVKFRELPC (SEQ ID NO: 60); RQLVVKFRAAPC (SEQ ID NO: 61); RQLVVKFRAIPC (SEQ ID NO: 62); RQLVVKFRAVPC (SEQ ID NO: 63); RQLVVKFRAEPC (SEQ ID NO: 64); RQLVVKFRVVPC (SEQ ID NO: 27); RQLVVKFREEPC (SEQ ID NO: 26); RQEEEKFREEPC (SEQ ID NO: 28); RQEEEFEEEPC (SEQ ID NO: 65); RQLVVKFRALXC (SEQ ID NO: 66); RQLVVKFRALPS (SEQ ID NO: 67); RQLVVKFRALPT (SEQ ID NO: 68); or RQLVVKFRALPX (SEQ ID NO: 69). The peptides disclosed above contain substitution(s) at various positions and were generated based on the 12-mer peptide of SEQ ID NO: 17 in consideration of the experimental results for characterizing the adhesiveness activity of the present peptides and thus it is evident that they also have the adhesiveness activity and thus are encompassed by the present disclosure.

In other embodiment, the present disclosure is related to polypeptides with SEQ ID NO: 1 to 69.

In still one embodiment, the present disclosure is related to an isolated polypeptide having an amino acid sequence as set forth in SEQ ID NO: 1, 6, 15-22, 24-27, 29-37, 42-64, 67 or 68.

In still other embodiment, the N-term amino acid of the present peptide comprising the peptide of formula III at the N-term is either R or K, positively charged residues or D or E, negatively charged residues Thus, also encompassed in the present disclosure are the peptides having a formula III-I, III-II-III-I-II, wherein the first amino acid residue is positively charged R or K. or negatively charged D or E.

In one embodiment, the present disclosure is related to an isolated polypeptide having an amino acid sequence set forth in SEQ ID NO: 15-20, 22, 24-27, 30-37, 42-64, 67 and 68, wherein the first amino acid (the amino acid at the N-term) is substituted with a lysine residue, the first amino acid of SEQ ID NO: 21 is substituted with an arginine, and the first amino acid of SEQ ID NO: 29 is substituted with an aspartic acid.

In other embodiment, the present peptides may have either a K or R as its first amino acid since from Table 1, it can be determined that the polypeptide having the first amino acid K (Lysine) as in SEQ ID NO: 21 and having the first amino acid R (Arginine) in other polypeptides are both working and further both Lys and Arg are positively charged amino acids, which are known to be interchangeable in the art and as described above in which Lys/Arg is described as interchangeable. Also it can be determined that the first amino acid can be either positively charged amino acid or negatively charged acid. Thus negatively charged amino acids Asp and Glu known to be interchangeable in the art can be substituted for each other.

Thus, in one embodiment, the first amino acid of SEQ ID NO: 15-20, 22, 24-27, 30-37, 42-64, 67 and 68 is substituted with a lysine residue, and the first amino acid of SEQ ID NO: 21 is substituted with an arginine, and the first amino acid of SEQ ID NO: 29 is substituted with an aspartic acid.

In still other embodiment, the first amino acid of SEQ ID NO: 15-22, 24-27, 30-37, 42-64, 67 and 68 is substituted with an aspartic acid or a glutamic acid residue, and the first amino acid of SEQ ID NO: 29 is substituted with a lysine or arginine residue.

Further In the present peptides, the first negatively charged or positively charged amino acids may be repeated up to 15mer. From Table 1, it can be determined from SEQ ID Nos 39, to 41 that the first Arg can be comprised more than one and up to 15, and still have adhesiveness. Thus it can be substituted with other positively charged amino acid, Lysine (K). Further the first amino acid can be negatively charged amino acid Glu or Asp, which thus may be comprised up to 15mer. Thus, in one embodiment, the amino acid sequence of SEQ ID NO: 15-20, 22, 24-27, 30-37, 42-64, 67 or 68 may further comprise up to 14 arginine residues at the N-terminus, the amino acid sequence of SEQ ID NO: 21 further comprises up to 14 lysine residues at the N-terminus, and the amino acid sequence of SEQ ID NO: 29 further comprises up to 14 glutamic acid residues.

In still other embodiment, the present disclosure is related to an isolated polypeptide having an amino acid sequence set forth in SEQ ID NO: 15-22, 24-27, 30-37, 42-64, 67 and 68, wherein the first amino acid of SEQ ID NO: 15-22, 24-27, 30-37, 42-64, 67 and 68 is substituted with an aspartic acid or a glutamic acid residue, and the first amino acid of SEQ ID NO: 29 is substituted with a lysine or arginine residue.

In still other embodiment, the present disclosure is related to an isolated polypeptide having an amino acid sequence set forth in SEQ ID NO: 15-22, 24-27, 30-37, 42-64, 67 and 68, wherein the amino acid sequence of SEQ ID NO: 15-20, 22, 24-27, 30-37, 42-64, 67 or 68 further comprises up to 14 arginine residues at the N-terminus, the amino acid sequence of SEQ ID NO: 21 further comprises up to 14 lysine residues at the N-terminus, and the amino acid sequence of SEQ ID NO:29 further comprises up to 14 glutamic acid residues.

However, the polypeptides according to the present invention are not limited to the above-described sequences, but include biological equivalents thereof. The term biological equivalents refer to polypeptides which contain additional modifications to the amino acid sequences disclosed herein, but have substantially the same or similar activity as the polypeptide disclosed herein. Such modifications include, for example, a deletion, insertion and/or substitution of one or more residues in the amino acid sequence. The modifications may be determined in consideration of properties of the similarity of side chains such as sizes, charges, hydrophobic or hydrophilicity. Based on the characteristics of the side chains in terms of size, shape and chemical/electrical properties, it is considered that arginine, lysine and histidine are positively charged residue; alanine, glycine, and serine are having similar size of side chains; phenylalanine, tryptophan and tyrosine are having similar structure of side chains. Thus, in consideration of this, arginine, lysine and histidine; alanine, glycine and serine; phenylalanine, tryptophan and tyrosine are considered biologically equivalent.

Also when introducing modifications, hydropathy indices may be considered. Each amino acids is endowed with a unique hydrophobic index according to its hydrophobicity and charges as follows: Isoleucine (+4.5); Valine (+4.2); Leucine (+3.8); Phenylalanine (+2.8); Cysteine/Cystine (+2.5); Methionine (+1.9); Alanine (+1.8); Glycine (−0.4); Threonine (−0.7); Serine (−0.8); Tryptophan (−0.9); Tyrosine (−1.3); Proline (−1.6); Histidine (−3.2); Glutamate (−3.5); Glutamine (−3.5); Aspartate (−3.5); Asparagine (−3.5); Lysine (−3.9); and Arginine (−4.5).

The hydropathy indices described as above are useful in imparting proteins with an interactive biological function. It is known that similar biological activities are obtained from substitutions with amino acid having similar hydrophobic index. When modifications are performed in reference to the hydrophobic index, it is preferable to select an amino acid for a substitution having a hydrophobic index difference within ±2, more preferably ±1, particularly more preferably ±0.5.

Also it is known that the substitutions between amino acids having similar hydrophilicity value result in biologically equivalent proteins.

For example, U.S. Pat. No. 4,554,101 may be referred, in which hydrophilic values are disclosed as follows: Arginine (+3.0); Lysine (+3.0); Aspartate (+3.0±1); Glutamate (+3.0±1); Serine (+0.3); Asparagine (+0.2); Glutamine (+0.2); Glycine (0); Threonine (−0.4); Proline (−0.5±1); Alanine (−0.5); Histidine (−0.5); Cysteine (−1.0); Methionine (−1.3); Valine (−1.5); Leucine (−1.8); Isoleucine (−1.8); Tyrosine (−2.3); Phenylalanine (−2.5); Tryptophan (−3.4).

Further, for amino acid substitutions that fall within the scope that does not result in a substantial change in the biological characteristics compared to a parent protein, H. Neurath, R. L. Hill, The Proteins, 3rd Edition, Academic Press, New York, 1979 may be referred. For example, typical substitutions include Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu and Asp/Gly.

Furthermore, when considering variants having biologically equivalent activities as described above, it is encompassed in the present invention not only the amino acid sequences disclosed herein or nucleic acids encoding the same as described below, also the sequences substantially identical to the sequences disclosed herein. The term "sequences substantially identical" refers to those showing preferably at least 61%, more preferably at least 70%, still more preferably at least 80%, most preferably at least 90% similarity to the sequence disclosed herein, when aligning sequences with the sequence disclosed herein so as to correspond to each other to the highest possible extent and analyzing the aligned sequences using algorithms that are generally used in the art. Methods of alignment of sequences for comparison are well-known in the art. Various programs and alignment algorithms are described in, for example, Smith and Waterman, *Adv. Appl. Math.* (1981) 2:482; Needleman and Wunsch, *J. Mol. Bio.* (1970) 48:443; Pearson and Lipman, *Methods in Mol. Biol.* (1988) 24: 307-31; Higgins and Sharp, *Gene* (1988) 73:237-44; Higgins and Sharp, *CABIOS* (1989) 5:151-3; Corpet et al., *Nuc. Acids Res.* (1988) 16:10881-90; Huang et al., *Comp. Appl. BioSci.* (1992) 8:155-65 and Pearson et al., *Meth. Mol. Biol.* (1994) 24:307-31. The NCBI Basic Local Alignment Search Tool (BLAST) (Altschul et al., *J. Mol. Biol.* (1990) 215:403-10) is available from the NBCI and the like, for use in connection with the sequence analysis programs such as blast, blastp, blasm, blastx, tblastn and tblastx. The BLAST can be accessed at www dot ncbi dot nlm dot nih dot gov forward slash BLAST forward slash. A description of how to determine sequence identity using this program is available at www dot ncbi dot nlm dot nih dot gov forward slash BLAST forward slash blash underscore help dot html.

In one embodiment, the present peptides also include ones having a conservative amino acid substitution(s) in the present peptides. The conservative substitution refers to a substitution without substantially affecting or changing the activity of the original peptides. The substitutions may be for example included at least one.

The conservative amino acid substitutions are known in the art, which may be referred to: Table 1 based on BLOcks Substitution Matrix; Creighton (1984) Proteins. W. H. Freeman and Company (Eds); and Henikoff, S.; Henikoff, J. G. (1992). "Amino Acid Substitution Matrices from Protein Blocks". PNAS 89 (22): 10915-10919. doi:10.1073/pnas.89.22.10915; WO2009012175 A1.

TABLE 1

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, Thr |
| Met | Leu; Ile | Gln, Ile, Leu, Val | Gln, Ile, Leu, Phe, Val |

TABLE 1-continued

| Original Residue | Very Highly - Conserved Substitutions | Highly Conserved Substitutions (from the Blosum90 Matrix) | Conserved Substitutions (from the Blosum65 Matrix) |
|---|---|---|---|
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Thus in one embodiment, the present peptides also includes ones having conservative amino acid substitution in the peptides represented by SEQ ID NO: 1 to 69.

In one embodiment, the C- and/or N-term, particularly C-term may be substituted with an inert or non-reactive group such as $NH_2$ group to increase the stability of the peptides.

The Composition Comprising the Present Peptides and its Uses

Other aspect of the present disclosure provides a composition comprising the peptides as described herein before, and its use as an adhesive.

The present adhesive peptides or the composition comprising the same are able to attach various materials to the surface of inorganic origin. In the present disclosure, inorganic materials or the surface of inorganic materials or the surface of inorganic origin are used interchangeably. Inorganic materials include materials within the generally accepted meaning which do not contain carbon, silicon or nitrogen, or have a relatively free electron configuration due to high degree of electrostatic conductivity. Particularly included in the present disclosure are inorganic materials having a hydrophobic surface such as metal for example iron, copper, noble metal including gold, silver or platinum, titanium, or aluminum; ceramics such as zirconia; calcium apatite crystals such as hydroxyl apatite; high molecular weight synthetic resins such as polyethylene and; glass and combinations thereof without being limited thereto.

The present adhesive peptides or the composition comprising the same are able to attach various materials of biological or non-biological origin to the surface of inorganic origin. The materials of non-biological origin include a metal, a glass, a plastic or synthetic polymer, and the materials of biological origin include cells, tissues, proteins, lipids, carbohydrates or nucleic acids or the combinations thereof.

The present adhesive peptides as disclosed herein can be attached or used to attach various materials of biological or non-biological origins or the surfaces thereof. Thus such properties may be used for mediating attachment among materials with same or different properties. For example, the attachments between a first inorganic surface and a second inorganic surface having same or different properties or between an inorganic material and materials of biological origins may be included. For example, the present adhesive peptides or the composition comprising the same enables the attachments between inorganic materials such as metals, plastics, synthetic polymers, or enables the attachments of biological materials such as cells, tissues, proteins or components of the cell walls of bacteria such as lipopolysaccharide as well as (1,3)-beta glucan, a cell wall component of the yeast, to the inorganic surface such as the culture plate.

Without being intended to be limited by this theory, the present peptides is found to increase the adhesiveness by having affinity to the peptidoglycan layers, and further to the components (lipopolysaccharide are included) of the cell walls of microorganisms as well as to (1,3)-beta glucan a component of yeast cell wall. Thus the present peptides can have wide applications in various fields.

Without being intended to be limited by this theory, the present peptides exhibit excellent affinity to proteoglycans, a component of cartilage. Thus the present peptides can be used advantageously in the field where the tissues attachments are required for tissue regeneration. the present adhesive peptide may be applied for attachment or used for coating materials or surfaces thereof classified as biological materials such as animal, plant and any parts therefrom, including for example, cells, tissues, and organs. The cells to which the present adhesive peptides or the composition comprising the same may be applied or used are not particularly limited and include cells from plants, insects and animals. For example, the cells include pluripotent cells, adult stem cells, progenitor cells. The examples of pluripotent cells include ES cells, GS cells, and iPS (induced pluripotent stem cells). The examples of adult stem cells includes MSC (mesenchymal stem cells), Hematopoietic stem cells, and nerve stem cells. The examples of precursor cells include cells from skin, dermis, endothelium, epidermis, muscle, myocardium, nerve, bone, cartilage, brain, epithelium, heart, kidney, pancreas, spleen, oral cavity, cornea or hair. The examples of cells from human includes but are not limited to ES cells, iPS cells, MSC, chondrocytes, osteoblasts, osteoclasts, mesenchymal cells, myocytes, myocardial cells, nerve cells, hepatocytes, embryonic cells, fibroblasts, corneal epithelial cells, corneal endothelial cells, vascular endothelial cells and hematopoietic cells. The cells may be autologous or heterologous.

Also the present peptides may be modified or functionalized with various compounds for example via an epsilon amino groups to link various functional group of interest.

The use of the present adhesive peptides or compositions as an adhesive include at least one inorganic surface and includes but is not limited to (1) adhesion between substrates in water (water or saline water); (2) orthopedic treatments such as bones, ligaments, tendons, meniscus and muscle treatment and artificial material implants; (3) treatment such as perforation, fissure, incision, or ophthalmic adhesions such as corneal transplantation, and artificial cornea insertion; (4) dental applications such as braces, machining dentures, crown mounting, teeth fixation, broken tooth treatment, and filler fixation; (5) surgical treatment such as vascular occlusion, cell tissue grafting, artificial material grafting, wound closure; (6) adhesions in plants such as plant graft, wound healing; (7) a cell or tissue culture comprising stem cells; (8) substrate materials for medical devices such as artificial organs, dental, surgical or ophthalmic devices, such as implants; bone removers, bone cages, guide wires, catheters and stents; (9) adhesion of bone, titanium or ceramic and the like; and (10) a bioconjugation of various biomaterials including bioactive agents, drugs, labeling agents and target materials to the surface of the bone, titania, or ceramics.

In one embodiment, the present adhesive peptides or the compositions comprising the same may be used in dental, ophthalmic or orthopedic treatment for cell or tissue graft or regeneration, in which case the surface onto which the present peptide or compositions may be applied include but is not limited to PLGA, hydroxyapatite, zirconium, titanium, iron, stainless steel, titanium, platinum, gold, and alloy.

In still other embodiment, the present adhesive peptides or the compositions comprising the same may be used for attaching cells to supports. The supports include but are not limited to cell culture plate, microbeads, substrate, tissue implants and the like. The present peptides or compositions may be used for cell or tissue cultures, particularly for stem cell cultures. According to one embodiment of the present disclosure, the present peptides are found to be very effective in attaching cells in comparison to currently used agents used for cell adhesion (refer to FIGS. 1, 2, 3, 4, 5 and 6 and the like).

The present adhesive peptides or the compositions comprising the same may be used in manner as generally known in the art. And the typical method is to apply the present peptides or composition to the surfaces. For example, commercial cell and tissue adhesive products such as CELL-TAK® (BD Biosciences, USA) may be referred for formulations, amount of use, usages.

The composition comprising the present peptides may be prepared in solvent type, water-soluble type or solvent free type and may be used in the amount of 0.1 to 1000 ng/mm$^2$, particularly 1 to 100 ng/mm$^2$ based on the area of the surfaces to be treated without being limited thereto.

The amount of the present compositions to be applied or the adhesiveness of the composition may be determined or controlled by treatment with surfactants, oxidizing agents, crosslinking agents, or fillers or by adjusting the concentration of the present peptides. For example the fillers may include but are not limited to collagen, hyaluronic acid, chondroitin sulfate, elastin, laminin, casein, hydroxyapatite, albumin, or fibronectin.

In other aspect, the present disclosure is related to the coating composition comprising the present peptide, particularly adhesive coating composition or protective coating composition, which includes for example, tapes, labels or protective films as used in everyday life. The adhesive of the present disclosure has a property of bonding between non-biological materials such as glass, plastic, polymer synthetic resin, or between non-biological material and biological material, so that it can be used as a coating material for such surfaces or substrates. Also due to its properties of water resistance, it is possible to prevent oxidation of the substrate by applying it to the surface of the substrate in an underwater environment. Examples of applications of the protective coating include, but are not limited to, application to a device or apparatus used in water such as a ship to prevent corrosion.

The adhesive, the composition or the coating agent according to the present disclosure may contain only the adhesive protein alone, but it may further comprise any of known adhesives, adhesive proteins other than the adhesive proteins of the present invention, or resins, organic solvents, antioxidants, corrosion inhibitors, coloring agents, and the like which are comprised in the known adhesives or coating agents. The amount of the additional components may be appropriately selected within a range normally permitted depending on the kind of the component and the formulation of the coating or adhesive agent. When an additional component is used, the adhesive protein, which is an active ingredient, is contained in an amount capable of maintaining the adhesive activity in the coating or adhesive agent, and may be included in, for example, 0.01 to 80% by weight of the adhesive or coating agent.

The composition for attaching or coating according to the present disclosure may be in the form of a cream, an aerosol (spray), a solid, a liquid or an oil, but is not limited to the above-mentioned formulations.

Methods

In other aspect, the present disclosure provides a method of preparing the composition described above comprising the step of providing a vector having a nucleic acid encoding the isolated polypeptide and expressing the vector in an appropriate cell.

In the previous method, the method may further comprise a step of isolating the polypeptide expressed in the cell.

With respect to the nucleotides encoding the peptides disclosed herein and vectors containing the same and cells transformed/transfected with the vector, one of ordinary skill in the art would be able to select appropriate vectors and cells to which the present nucleotides are cloned and delivered, respectively. One of ordinary skill in the art would be able to determine the nucleotides sequences encoding the present peptides without undue experimentation based on the known codon table and codon degeneracy and codon preferences. For example nucleotide sequences encoding SEQ ID NO: 1 and 17 peptides may be represented by CARYTNGTNGTNAAR (SEQ ID NO: 70); and MNGCARYTNG TNGTNAARTT YMNGGCNYTN CCNTGY (SEQ ID NO: 71), respectively in which R=A,G; K=G,T; H=A,C,T; D=A,G,T Y=C,T; S=C,G; B=C,G,T; N=A,G,C,T; M=A,C; W=A,T; V=A,C,G.

In another aspect, the present disclosure is also directed to a method of attaching two or more materials or the surfaces thereof using an adhesive composition according to the disclosure herein.

In one embodiment, the method according to the present disclosure includes the steps of treating an adhesive according to the invention to a first material and/or a second material; and contacting the two materials in a condition sufficient to allow the adhesion between the two materials to occur.

In one embodiment, the at least one of the first material or the second material is an inorganic surface.

The sufficient conditions will vary depending on the kind of the specific material used for the adhesion, and those skilled in the art will be able to determine appropriate conditions, for example, temperature, and time or the composition of the medium in which adhesion occurs and the like in consideration of the present disclosure including Examples, and the knowledge known in the related art.

The first material or the second material according to the present invention may be treated in whole or in part, or both first and second materials or the first or the second material may be treated in Whole or in part. In one embodiment, the adhesive or composition is applied on an inorganic surface, such as a cell culture dish, and cells are added to the cell culture dish so as to attach them to the dish. In another embodiment the adhesive or composition according to the present invention may be added to the culture medium containing the cells which are then added to the cell culture dish. In another embodiment, an inorganic surface, for example a commercialized bone graft, can be coated with an adhesive according to the present invention and a biological material such as an osteogenic protein can be attached thereto. Or a biologic material may be conjugated to the present peptides which are then attached to the inorganic surface.

For other inorganic surfaces or materials which can be attached thereto, reference may be made to the foregoing description.

Hereinafter, the present invention will be described in further detail with reference to examples. It is to be understood, however, that these examples are for illustrative purposes only and are not intended to limit the scope of the present invention.

EXAMPLES

Example 1. Preparation of the Present Peptides

The peptides used in the Examples were synthesized by 9-fluorenylmethyloxycarbonyl (Fmoc) method (Lugen Sci, Korea; Peptron, Korea). To confirm the reproducibility of the experimental results using the peptides, identical sets of peptides were independently synthesized 2 or 3 times from Lugen Sci and Peptron, respectively. Consistent results were obtained from the peptides synthesized from different companies and among different batches.

Example 2. Analysis of the Present Peptide for Conjugating Fluorescent Materials and Analysis of the Adhesiveness Thereof to Various Non-Biological Origin Surfaces One of the peptides synthesized in Example 1, A7-1 (RQLVVKFRALPC; SEQ ID NO: 17)(corresponding to 12mer (A) of Table 1) was conjugated to a biotin (Thermo Scientific, USA) or a FITC (Sigma, USA) to a cysteine residue via —SH group, which were then used to treat a glass., PCL, Ti, Col, Zr, vinyl, and PS fiber (concentration 10 μM in PBS, adsorption for 20 min at RT followed by washing one with PBS). The adsorption was analyzed by a FITC fluorescent image analyzer LAS (Fuji, Japan). To liberate the biotin from the peptides, the conjugated peptides were treated with DTT (100 mM in PBS, 20 min at RT followed by washing one time with PBS). As a control, dyes were used alone.

Results are shown in FIGS. 1A to 1D. As shown there, it was found that the biotins are strongly attached through the present peptide to the surface of the material employed. Particularly the attachment was disappeared by treating the surface with DTT (FIG. 1A). This confirms that the biotin and FITC were attached to the surfaces through the present peptide.

Example 3. Analysis of the Present Peptide for the Adhesiveness to Various Materials of Biological or Non-Biological Origin Experiments basically the same as Example 2 were performed except that bone grafting material BIO-OSS® (Geistlich Pharma, Inc) and MBCP™ (Biomatlante), a widely used bone graft, were used instead of the glass. The conditions were as follows: BIO-OSS® particles were reacted with 10 μM of the present peptide conjugated with FITC for 10 min at RT, which was then washed 5 times for 48 hrs in PBS containing 0.05% TWEEN®-20 and analyzed by a confocal microscope (Zeiss LSM-700 model with Zen 2011 software, x20).

Also, to confirm the adhesiveness of the present peptide in in-vivo environment, the present peptides were injected into various tissues and the thin sections were prepared from the tissues for analysis. Specifically, 10-20 μl of A7-1 of the present peptide not conjugated or conjugated with Cys or FITC dye, or Cys or FITC dye alone at the concentration of 10 μM dissolved in PBS were administered to various tissues by injection or local application. Two hours after the administration, the mice were sacrificed and the tissues were harvested. The tissues were then washed three times in PBS for 30 min and thin sections were prepared therefrom and analyzed by a confocal microscope.

Figure 2A:
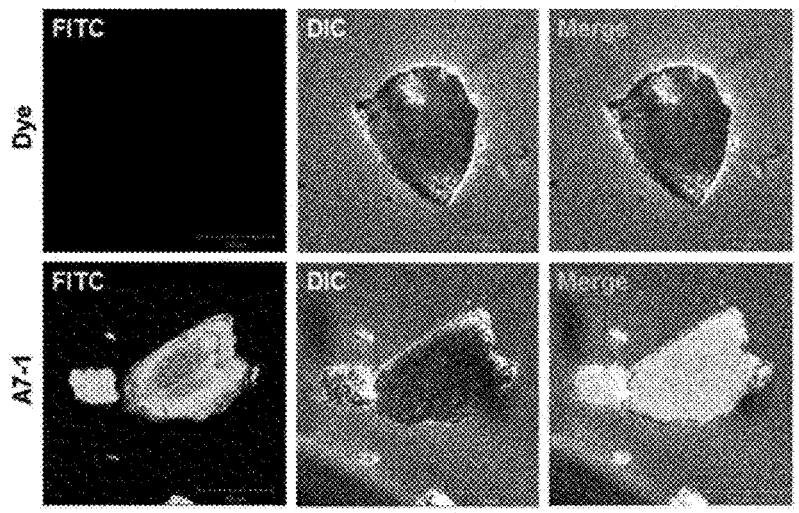
FIG. 2A is the results of testing the adhesiveness of the present peptide conjugated to FITC to the surface of bone graft BIO-OSS® (Geistlich Pharma, Inc), showing the excellent adhesiveness of the present peptide to a commercial bone graft.
Figure 2B:
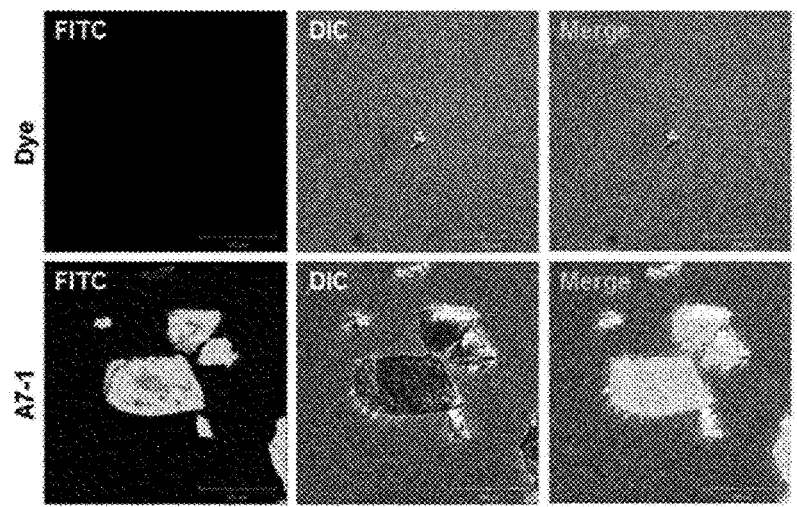
FIG. 2B is the results of testing the adhesiveness of the present peptide conjugated to FITC to the surface of bone graft MBCP™ (Biomatlante) and shows the excellent adhesiveness of the present peptide to a commercial bone graft. The fluorescent microscope image was taken at X200.
Figure 3A:
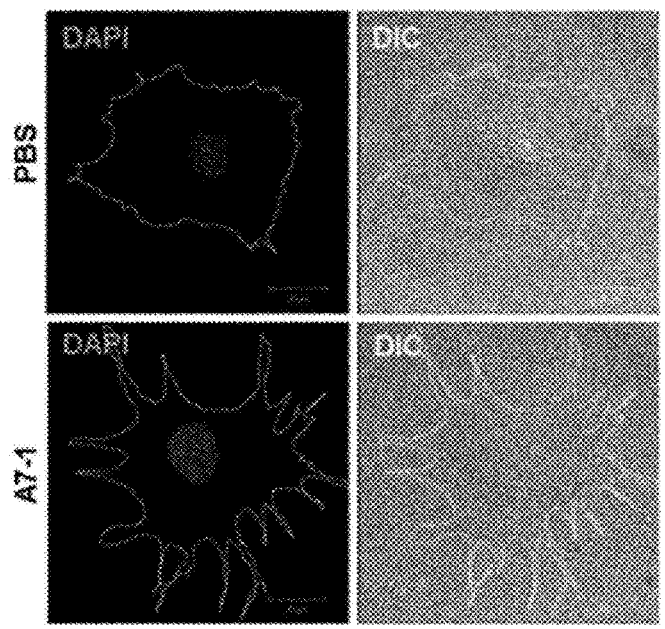
FIG. 3A is the results of testing the ability of the present peptide to increase the adhesiveness of anchorage dependent cell MC3T3-E1 to culture plates. The results show that the cells treated with the present peptide have a rough membrane boundary compared to negative control treated with PBS only. This indicates that the present peptide can increase the adhesiveness of biological materials such as cells to non-biological materials such as culture plates.
Figure 3B:
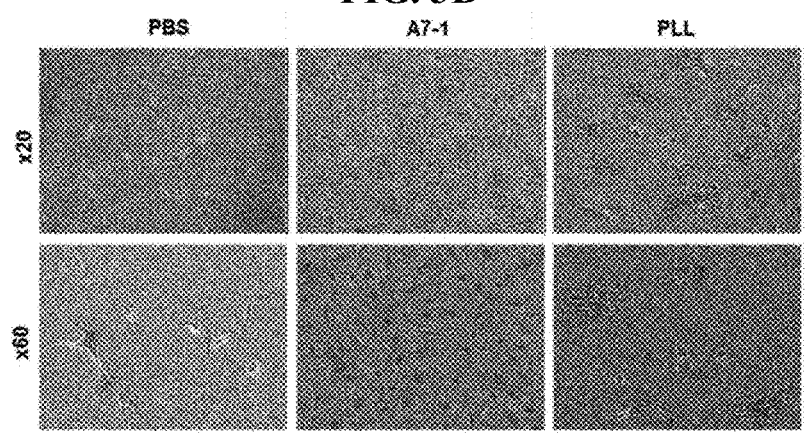
FIG. 3B is the results of testing the adhesiveness of anchorage dependent cell MC3T3-E1 treated with the present peptide to hydrophobic culture plates in comparison to those treated with PLL (poly-L-lysin) currently used to increase the adhesiveness of cells. The results show that the cells treated with the present peptides have increased adhesiveness in comparison to the cells treated with PBS or PLL. This indicates that the present peptides can have an industrial applicability by complement the low adhesiveness of various currently used tissue implant material such as PCL.
Figure 3C:
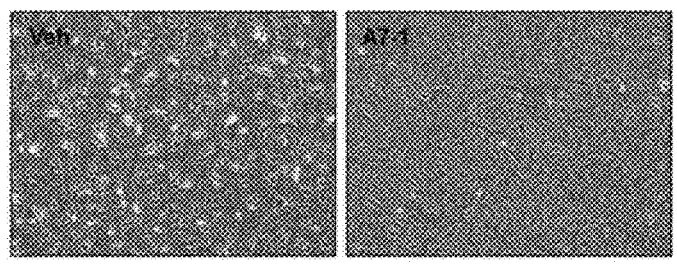
FIG. 3C is the results of testing the adhesiveness of anchorage dependent cell ST2 treated with the present peptide to hydrophobic culture plates in comparison to control treated only with a buffer. The results show that the cells treated with the present peptide have an increased adhesiveness compared to the control as shown by the fluorescent miscopy analysis.
Figure 3D:
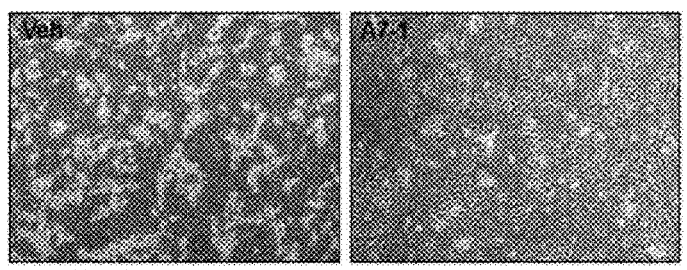
FIG. 3D is the results of testing the adhesiveness of anchorage dependent cell C2C12 treated with the present peptide to culture plates after the cells were thawed from freezing. The results show that the cells treated with the present peptide have an increased adhesiveness compared to the control as shown by the fluorescent miscopy analysis. Particularly the adhesiveness of cells after thawing is known to have great impact on the survival of the cells. The results indicate that the present peptides can be advantageously used in the field of cell culture particularly in the field of primary cell culture, by minimizing the cell death after the cells are thawed.
Figure 3E:
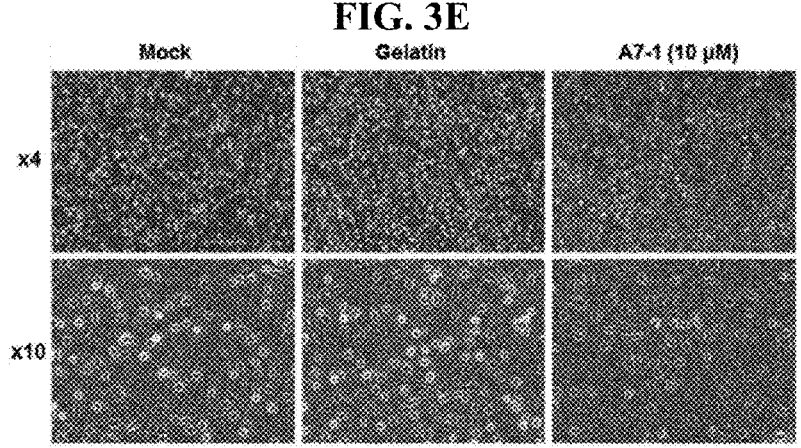
FIG. 3E is the results of testing the adhesiveness of mitomycin treated STO feeder cells treated with the present peptide to hydrophilic culture plates in comparison to a Mock as a negative control and gelatin. The results show that the cells treated with the present peptide have an increased adhesiveness compared to the negative control and gelatin control as shown by the fluorescent miscopy analysis.
Figure 3F:
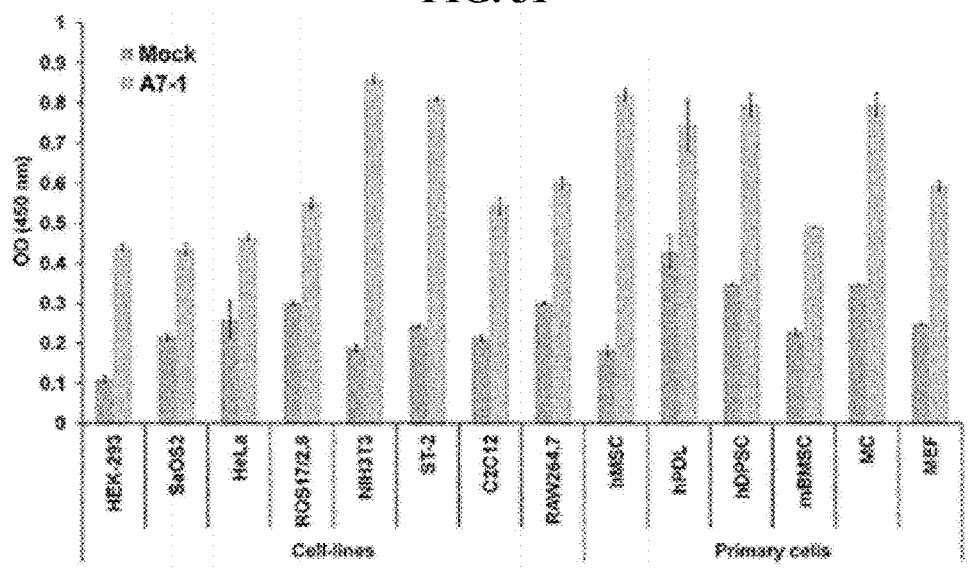
FIG. 3F is the results of testing the ability of the present peptide to increase the adhesiveness of various cells (established cell lines and primary cells) as indicated in the figure to hydrophobic culture plates in comparison to negative control (Mock). The results were analyzed by measuring the cell metabolism. The results show that the present peptide can increase the adhesiveness of various cells compared to the negative control.

Results are shown in FIGS. 2A and 2B, which indicate that the present peptides are able to attach to various materials from biological and non-biological origin to the surface of inorganic materials. The results show that the present peptide has an excellent adhesiveness to a commercial bone graft.

Example 4. Improvement of Cell Attachment to Inorganic Surfaces by the Present Peptides Materials used in the present Example are as follows: 10 mM peptide solution in PBS (Stock solution); plastic hydrophobic cell culture plate of 35 mm in diameter (for cell culture, Corning); DMEM (Dulbecco Modified Eagle Medium, cell culture medium: Hyclone); Fetal bovine serum (Hyclone); and C2C12 (mouse myoblast, cell, ATCC, CRL-1772); MC3T3-E1 (Mouse C57BL/6 calvaria cell, ATCC, CRL-2593) and ST2 (bone marrow-derived stroma cell: EMBO J. 7:1337?1343, 1983); STO (feeder cell: ATCC, CRL-1503), HEK-293 (ATCC, CRL-1573), SaO52 (ATCC, HTB-85), HeLa (ATCC, CCL-2), ROS17/2.8, NIH3T3 (ATCC, CRL-1658), RAW264.7 (ATCC, TIB-71), hMSC (Lonza, PT-2501), hPDL (HPLF) (Sciencell, Cat. #2630), hDPSC (isolated from human tissue according to Cells Tissues Organs 184: 105-16), mBMSC (Primary Bone Marrow Stromal Cell from mouse), MC (Primary Mouse Calvaria cell), MEF (Mouse Embryonic Fibroblast)

Experiments were done as described below.

The effect of the present peptide on the cell attachments was examined either by using a culture plate pre-coated with the present peptide or by adding the present peptide directly to a medium. Both methods produced the same results. For preparing the plates pre-coated with the present peptide, the present peptide was added to PBS or cell medium without FBS, which was then used to coat culture plates for 30 min and removed. Then cells were added thereto and the cells' attachment to the plates were measured for various times. Also for testing the present peptide by adding directly in medium, the present peptide was added when cells were suspended in the medium just before adding them to the plates. The cell attachments were measured as described below. Cells not treated with the present peptide were used as a negative control. And cells cultured in the plates treated with PBS or poly-L-lysin were used as a positive control. Cells were then examined by optical microscopy or confocal microcopy for overall examination of the cells, actin filament structure of the cells and irregularity of marginal shape of the cell membrane, for which the cells were stained for F-actin. Further to quantify the attachment, DNA amount of cell's metabolism were measured. The metabolism was determined by measuring absorbance using CK-8 (Dojindo), and DNA amount was determined by measuring fluorescence using Picogreen assay kit (Life Technologies) according to the manufacturer's instruction. To only use the cells attached for DNA amount and cell metabolism, the cells which were not attached were discarded by washing 2 times with PBS Results are shown in FIG. 3A to 3F. As shown there, the present peptide is able to increase the attachment of various types of anchorage dependent cells from primary cells, established cells, freeze and thawed cells and feeder cells, and shows a superior effect compared to PLL a material previously known for cell attachment. The conventional adhesives are usually recommended to use at the concentration of 0.32 to 1.6 µg/ml. However the present adhesive peptide is used at a much lower concentration of 0.32 to 1.6 µg/ml. Furthermore, conventionally used adhesives such as PLL, PDL (D-form), and PLO (poly-L-ornithine) are known to be toxic to the cells, which thus requires an intensive washing to remove residual adhesives after the coating. However, the present peptides are not toxic and safe to use by adding/mixing the peptides directly to the cell culture media as described above.

Example 5. Characterization of Mechanism of the Present Adhesive Peptide

The following experiments were done to identify the mechanism of the adhesiveness of the present peptide.

(1) Determination of the Requirement of Protein Synthesis

Firstly, Cells were treated with EDTA or cyclohexamide (CHX) known to prevent the protein synthesis (10 µM, 37° C. for 1 hr) or GAC as described above and tested for the adhesiveness.

Figure 4A:
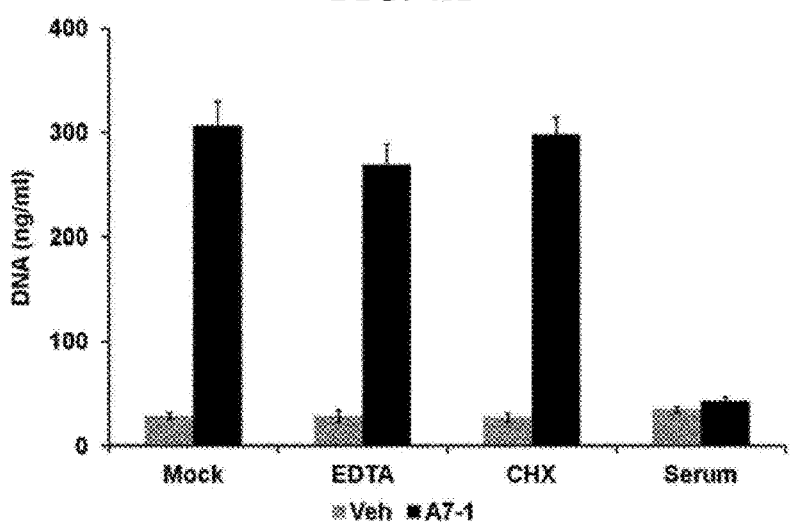
FIGS. 4A to 4C show the analysis results of testing the possible mechanism of the present peptide to increase the adhesiveness of cells.

Results are shown in FIG. 4A. From the figures, it is observed that EDTA or CHX does not affect the adhesiveness of the cells. Namely, it can be suggested that the adhesiveness exhibited by A7-1 of the present peptide does not requires the presence of electrolytes (result from EDTA) on the cell surface or new protein synthesis (result from CHX. One the other hand, it is observed that the serum inhibits the adhesiveness of the cells at early stage, which can be attributed to the binding of various types of GAG abundantly present in the serum to the present peptide. The change in the concentration of GAG present in the serum is known to be associated with development of various diseases (Volpi N. et al., Biochim Biophys Acta. (1995) Vol. 18: 49-58; Komosinska-Vassev K. et al., Clin Chim Acta. (2003) Vol. 331: 97-102; Anttonen A. et al., Lung Cancer. (2003) Vol. 41: 171-7; Fuster M. M. et al., Nat Rev Cancer. (2005) Vol. 5: 526-42; Hong Lu et al., 2010. Glycobiol. Insights Vol. 2: 13-28; Anower-E-Khuda M. F. et al., Glycobiology. (2013) Vol. 23: 865-76; Ibrahim S. A. et al., J. of Medical Lab. & Diagnosis (2013) Vol. 4: 8-20). Accordingly, this indicates that the present peptides can be used advantageously as an agent for regulating concentration of GAG in blood or an agent to targeting GAG. Also the results show that the present peptides exhibit its function of improving the adhesiveness of the cells not through the interaction with proteins in the cell membrane.

(2) Determination of the Involvement of Non-Proteinous Material

In this experiments, the involvement of non-proteinous material was determined. For this, the involvement of proteoglycans which are contained in ECM (Extracellular Matrix) in large amount were tested.

The Molecular Affinity of the Present Peptide to Proteoglycan

GAGs (glycosaminoglycan) such as heparan sulfate, heparin, chondroitin sulfate, dermatan sulfate, keratan sulfate and the like, the major components of proteoglycan, are main components of ECM and help maintaining the morphology of cells by maintaining the structural integrity of ECM. Further they are known to regulate the cells' adhesiveness and polarity. Such functions exhibited by ECM help the cells to adapt to the environment as well as regulate the physiology of the cells because of their direct involvement in a series of complex metabolism in the cells. The affinity of the present peptides to proteoglycans were tested by the following three experiments: (i) affinity chromatography; (ii) cell attachment analysis through competitive binding assay using purified GAG; (iii) analysis of inhibition of cell attachment by enzymes specifically breaking down ECM comprising GAG components. In the case of enzyme treatment, hyaluronidase (Sigma) and Collagenase (Sigma) were used. As purified GAGs, yaluronan (Sigma), chondroitin sulfate (Sigma), eparin (Sigma), heparan sulfate (Sigma) were used.

(i) Analysis of the interaction of the present peptide-haparin, or peptide-N-acetylglucosamin (GlcNAc) by affinity chromatography For chromatography, heparin-agarose beads (Biovision) and GlcNAc-agarose beads (Sigma) were used. 10 ng of FITC labelled peptide (F-peptide) was mixed in PBS-T buffer with heparin-agarose beads and GlcNAc-agarose beads, each precoated with BSA, and incubated at RT for 10 min. Then the mixture was washed 3 times with PBS-T buffer and resuspended in PBS for fluorescent measurement. For competitive binding experiments, the present peptide not labelled with FITC (Cold) was added to the mixture at various ratios of 1:1, 1:10 (10 times) and 1:100 (100 times) and allowed for incubation followed by fluorescent measurement. As a negative control, only FITC dyes were used to react with the beads. Further fluorescent signals from a sample containing just beads suspended in PBS were used as a blank. The results of FIG. 4B show that the present peptide has a strong affinity to heparin and GlcNAc, a component of GAG.

(ii) Analysis of the effect of GAG on the cell adhesiveness by competitive binding using purified GAG.

Figure 4B:
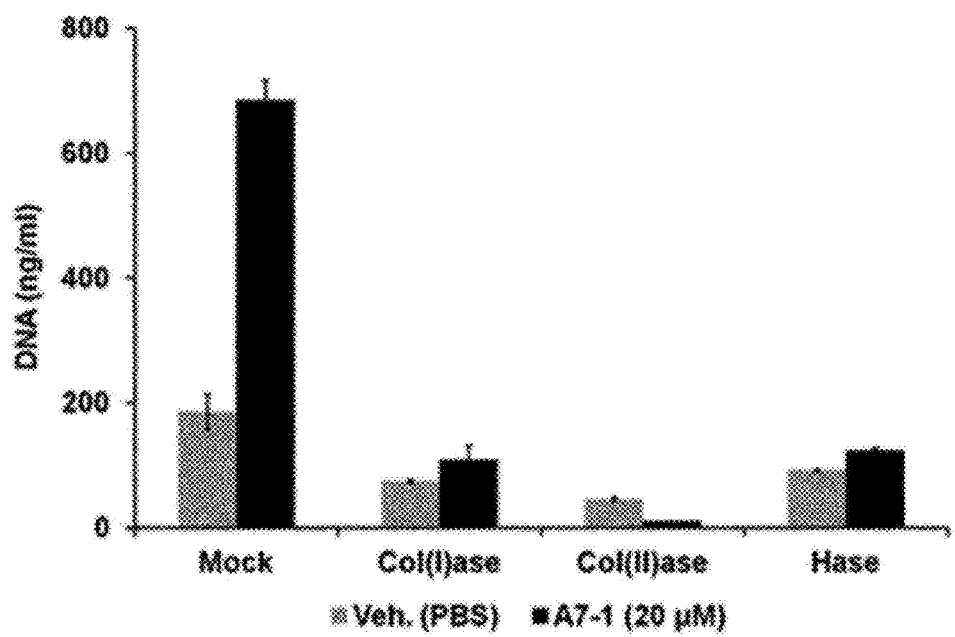
Figure 4B:
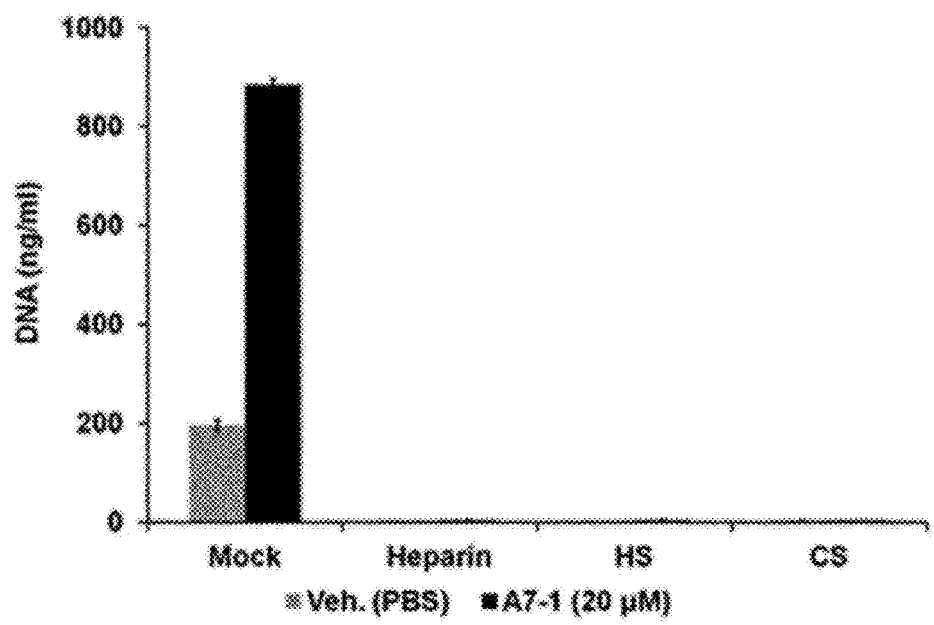

The results of FIG. 4B shows the inhibition of the adhesiveness of the present peptide by treatment with GAGs in a competitive manner indicating that the adhesiveness of the present peptides are inhibited by the addition of heparin, heparan sulfate, or chondroitin sulfate.

(iii) Inhibition of the improvement of the adhesiveness exhibited by the present peptide by use of enzymes specifically digesting ECM which contains GAG: Not only proteoglycans constituting ECM but also fibril proteins including collagen and the like all include GAGs as one of their components. When collagens comprising GAGs were hydrolyzed by use of collagenase, or hyaluronidases were used to hydrolyze hyaluronans, it is found that they all inhibit the adhesiveness of the present peptide. This also indicates that the cell adhesiveness exhibited by the present peptide is correlated with GAG Experiments were done as follows: (i) for competitive inhibition by treatment with purified GAG, GAG was added to cell suspension treated with trypsin at the concentration of 5 mg/ml and incubated at 37° C. for 10 min, which was then transferred to a culture dish coated with the present peptide and incubated for 30 min. After that, the amount of DNA contained in the attached cells was quantified to measure the adhesiveness. The quantification of DNA was performed by picogreen assay kit (Life Technologies); (ii) for assaying the effect of collagenase and hyaluronidase on the adhesiveness, cells treated with trypsin were suspended in a medium not containing fetal bovine serum and the enzymes were added thereto followed by incubation at 37° C. for 30 min. The enzymes were used at the concentration of 10,000 unit/$10^3$ cells. After the incubation with the enzyme, the enzymes were inactivated by adding EDTA and FBS. The cells were then centrifuged and resuspended in a fresh medium and incubated for 2 hrs. The attached cells were washed 2 times with PBS and harvested for DNA quantification by picogreen assay.

Results are shown in FIG. 4B. From the figure, it is observed that the present peptide has a strong affinity to proteoglycans, which is a major component of cartilage tissue, indicating that the present peptide can be used advantageously for tissue regeneration, and for clinical application in the field of plastic surgery and the like. Thus the excellent affinity to proteoglycan layers of the tissues such as cartilages indicates the usefulness of the present peptide for tissue regeneration and drug delivery.

(3) Comparative Experiment with RGDs

The present peptide A7-1 (10 μM) or A7-1 together with soluble RGDs peptide (0, 10, 100 and 1000 μM) for competition assay were added to anchorage dependent cells MC3T3-E1 in a test tube and incubated for 10 min. Then the cells were transferred to a culture plate and incubated for 10 min in a thermostatic incubator to allow the cells to attach. After 10 min, the medium was removed and the cells were washed 2 times with PBS to remove any unattached cells and a fresh medium without the peptide and CCK-8 (Dojindo) were added to the cells and incubated for 1 hr in a thermostatic incubator. Then the absorbance was measured at 450 nm. The medium mixed with CCK-8 only was used as a blank.

Figure 4C:
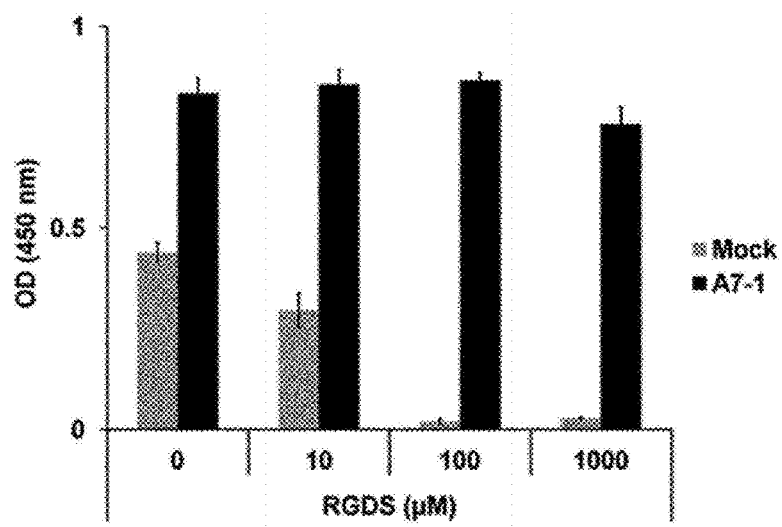

Results are shown in FIG. 4C. From the figure, when RGDs peptides are used alone, it is observed that the adhesiveness of the cells is decreased in a concentration dependent manner. In contrast, when the A7-1 and RGD peptide are used competitively, it is observed that the soluble RGD significantly decreases the adhesiveness of the cells to the bottom (substrate) by binding to integrin in the group not treated with A7-1. In the A7-1 treated group, it is observed that the adhesiveness of the cells is not affected at all. This indicates that the present peptide increases adhesiveness of cells by a mechanism different from that of RGD, in which RGD promotes the attachment of anchorage dependent cells through an interaction with integrin.

The results suggest that the present peptides have mechanical characteristics distinctive from RGD, the use of which are well established in the field of cell attachment and tissue regeneration, but the effectiveness of which are known to be not good in the related field. Thus the present peptides can be advantageously used substituting RGDs.

Example 6. Improvement of the Attachment of Embryonic Stem Cells to the Inorganic Surfaces Using the Present Peptides The present peptides were used to coat the culture plate or prepare nanostructure at the concentration level of 100 μM to investigate the attachment and pluripotency of induced pluripotent stem cells and human embryonic stem cells.

Human embryonic stem cells were cultured in hESC-media (with composition generally used in the related field), mTeSR (hES specific medium purchased from Stem cell technology), Essential 8 (hES specific medium purchased from Gibco BRL) and a medium only containing 10 ng/ml bFGF without any serum (to exclude the possible inhibition of the attachment of the cells by serum) to test the compatibility of the present peptide with various media currently used. Further the cells were analyzed by culturing cells in a colony state and by culturing cells in a single cell state by treating cells with 0.25% trypsin-EDTA. To test the effect of culturing ESC or iPSC in a feeder-free condition, MATRIGEL® (hESC) and gelatin (miPSC) were used as positive controls for comparison. The cells were also cultured in the presence of feeder cells as positive controls.

Figure 5A:
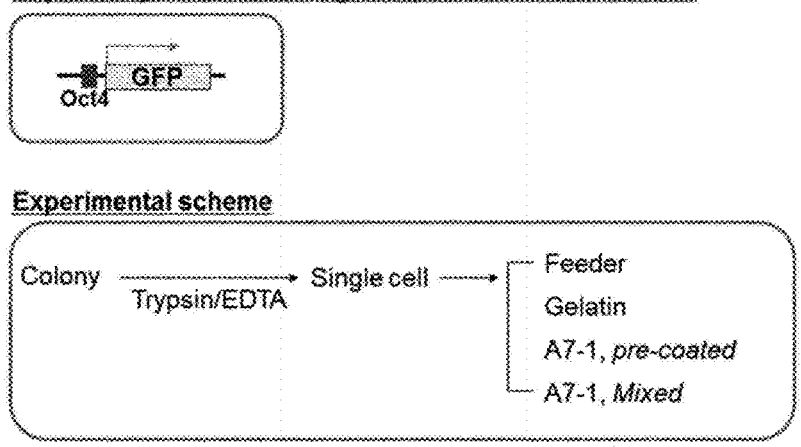
FIG. 5A is a schematic diagram of a reporter system and experimental process capable of testing the activity of Oct4, an indicator of sternness, to analyze the present peptide to promote the adhesiveness of iPSC (induced pluripotent stem cell)

The cells were analyzed by utilizing a plasmid (Szabo et al., 2002, Mechanisms of Development Vol. 115: 157-160) as shown in FIG. 5A able to detect the activity of Oct4 gene, a marker for sternness of embryonic stem cells (FIG. 5). Also other makers for sternness, the expression of Alp and Nanog genes were detected by staining with antibodies specific to each of the marker and examined by fluorescent microscope. Also the improvement of the cell attachment in hES cell culture was examined (FIG. 6).

Figure 5B:
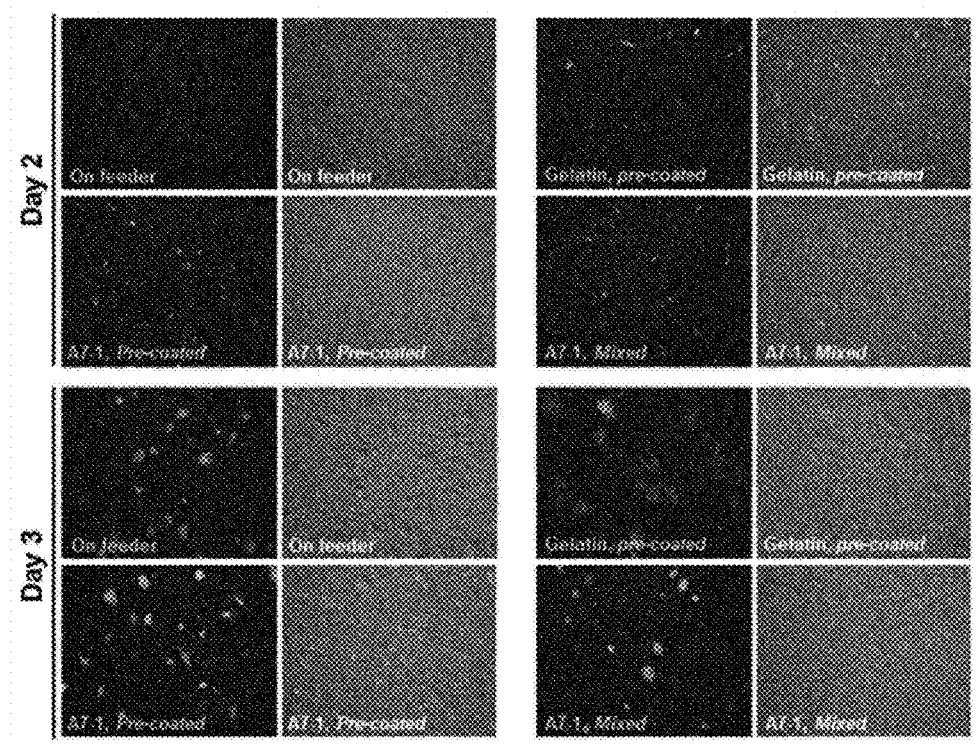
FIG. 5B is the results obtained using the system of FIG. 5A, in which the expression of Oct4 was examined at day 2 and 3 of the culture to analyze the sternness and adhesiveness of iPSCs in the presence or absence of the present peptides. In the experiment, the culture plates pre-coated with feeder cells or gelatin were used as controls and the present peptides were tested by pre-coating culture plates and adding or mixing the peptide in the cell medium. As a result, it is found that in the presence of the present peptides, the sternness and adhesiveness of iPSCs are well maintained in both tests of adding the peptides in the culture medium and pre-coating the plates.
Figure 5C:
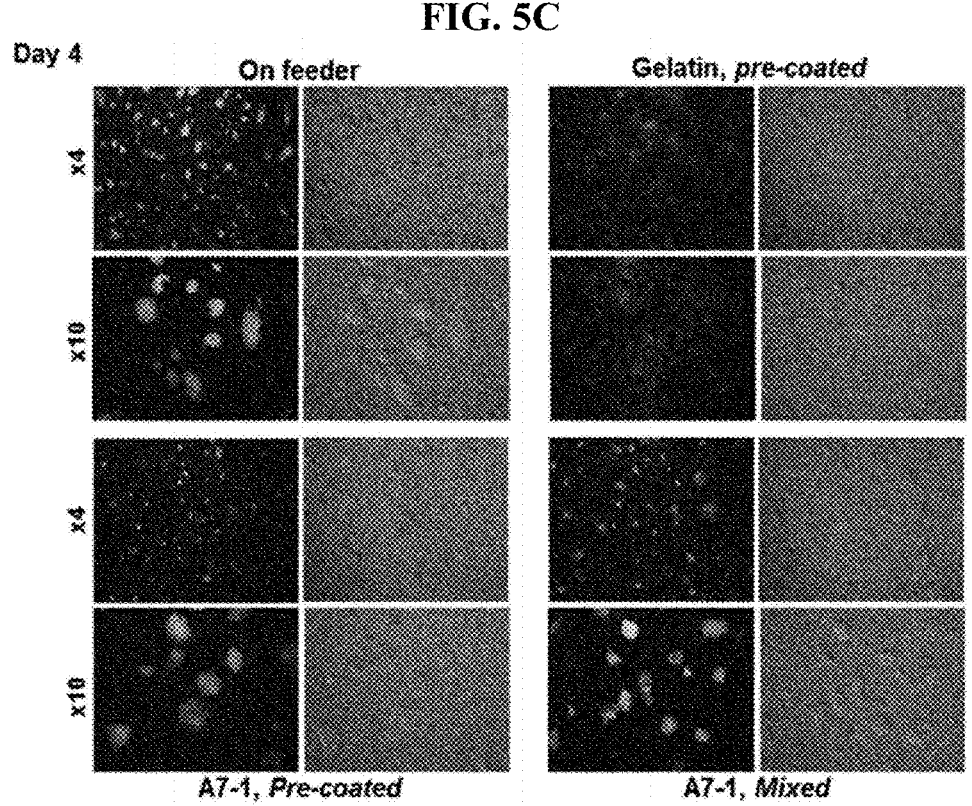
FIG. 5C is the results of experiment done as described in FIG. 5B except that the cells were examined at day 4. The result indicates that the sternness and adhesiveness of iPSCs are well maintained in the presence of the present peptides.
Figure 6A:
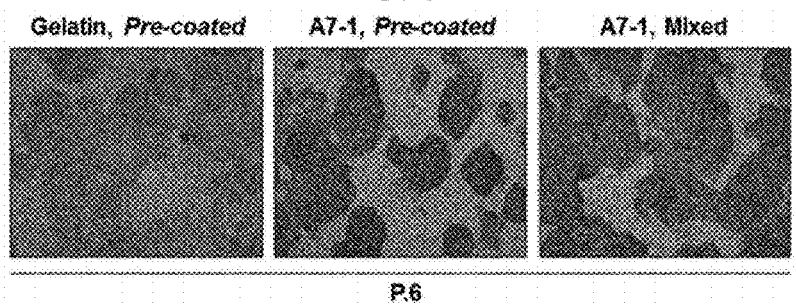
FIG. 6A is the results of experiments using Alp (alkaline phosphotase) as another sternness marker, which was analyzed by staining the cells for that marker. The results also indicate that the present peptides are able to mediate the adhesiveness of iPSCs and at the same time to maintain the sternness in both tests of pre-coating the plate and adding the peptide in the culture medium.
Figure 6B:
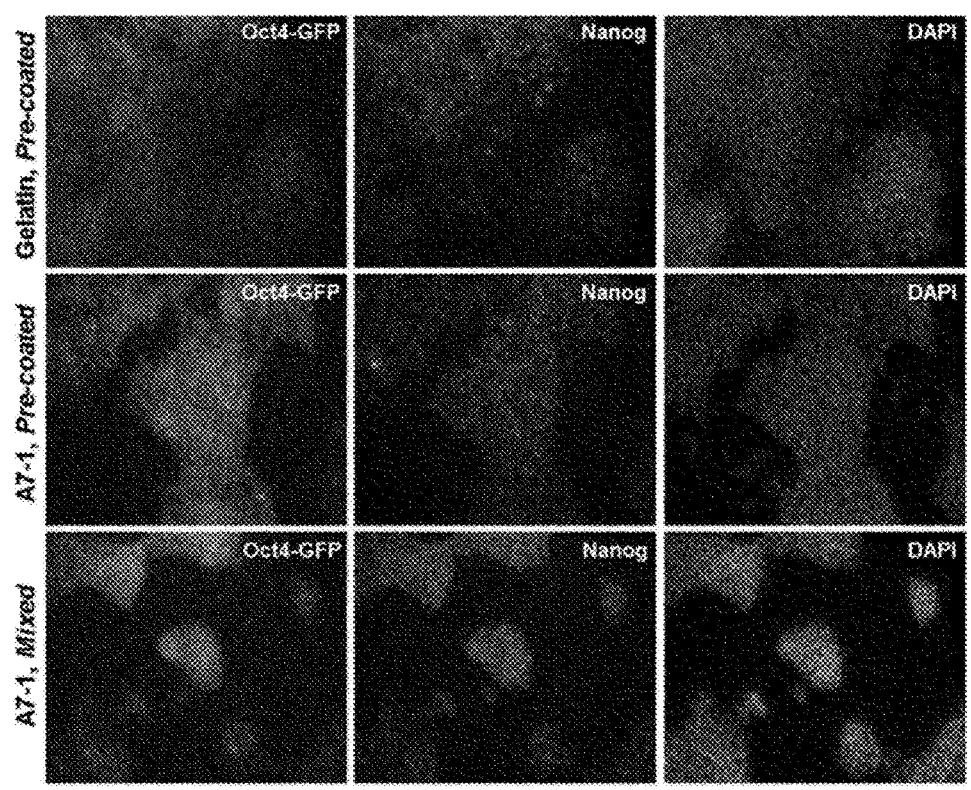
FIG. 6B is the results of experiments using Nanog as another sternness marker, which was analyzed by staining the cells for that marker. The results also indicate that the present peptides are able to mediate the adhesiveness of iPSCs and to maintain the sternness in both cases of pre-coating the plate and adding the peptide in a culture medium.
Figure 6C:
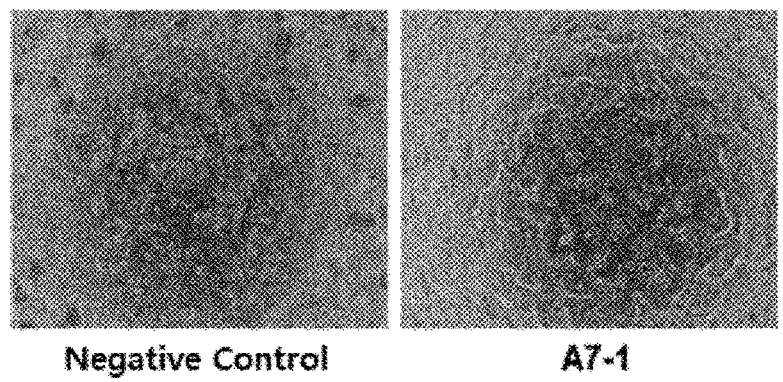
FIG. 6C the results of experiment done as described in FIG. 6A except that hESCs were used. The results indicate that the cells are able to proliferate well in the absence of feeder cells or MATRIGEL®.

Results are shown in FIGS. 5 and 6. In FIG. 5, it is observed that the present peptide is able to mediate the attachment of iPSC and maintain the sternness of the cells whether it is used to pre-coat the plate or is mixed in the medium (FIG. 5B). Further at day 4 of the culture, the effect of iPSC attachment and of maintenance of sternness is observed (FIG. 5C). Also as shown in FIGS. 6A and 6B by the expression of Oct4 and Nanog, the present peptides is able to mediate the attachment of iPSC and maintain the sternness of the cells whether it is used to pre-coat the plate or is mixed in the medium. The same results were obtained in the experiments using hESC in which the cells can grow by attachment and maintain the sternness by the present peptide and without the use of feeder cells or MATRIGEL® and the sternness (FIG. 6C).

Example 7. Bio-Conjugation of a Protein to an Inorganic Surface Via the Present Peptide The following materials were used in the present Example: the present peptide synthesized as described in Example 1 was used at the concentration of 10 μM in PBS; plastic culture plate having an area of 1.9 cm$^2$ (24-well plate, Corning); DSS (Disuccinimidyl suberate, $C_{16}H_{20}N_2O_8$, Thermo Scientific Inc.); recombinant human BMP2 (rh-BMP2, BD bioscience); DMSO (Dimethyl sulfoxide for dissolving DSS, Sigma-Aldrich); Tris-HCl, pH7.0 (Stop solution); PBS (phosphate buffered saline, reaction solution).

Figure 7A:
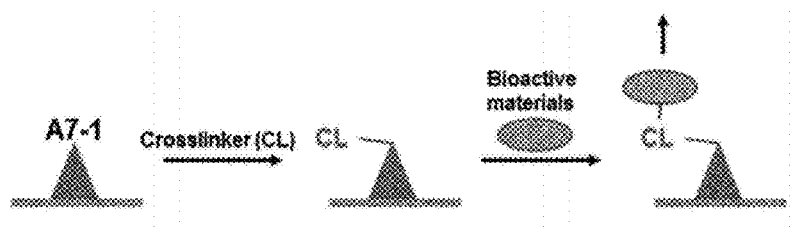
FIG. 7A is a schematic representation of a process attaching a therapeutic protein such as BMP using the present peptides, in which the present peptide is conjugated to a bioactive material such as BMP having activity on a inorganic surface via a cross linker.

The schematic diagram explaining an analysis logic is shown in FIG. 7A. As shown in FIG. 7A, when the present peptide can be conjugated to a therapeutic protein with a desired activity such as BMP via cross linker, due to the adhesiveness of the present peptide, the local concentration of the therapeutic protein can be effectively increased and thus maximizing the therapeutic effect.

The experimental methods are as follows. Peptide-rh-BMP2 covalent bond (Cross-linking) reaction was performed basically as described in the manufacturer's (Cross-linker) methods. Brief summarization is as follows: (i) peptide coating: 200 μl of the peptide solution (10 μM in PBS as prepared in Example 1) was dispensed into a cell culture plate and allowed to adsorb to the plate for 18 hrs at 4° C.; (ii) DSS-BMP2 complex formation: 20 molar excess of DDS relative to rhBMP2 was allowed to form covalent bonds in a total volume of 100 μl reaction solution for 1 hr. The concentration of rhBMP2 was used at the concentration of 300 ng per 1.9 cm$^2$. In this case, the culture plates coated with each of DSS, rhBMP2, and DSS-rhBMP2 were used as negative controls because it was observed that they were significantly removed during the washing step due their lack of adhesiveness to the surface of the plate; (iii) Peptide-DSS-BMP2 complex formation:100 μl of DSS-BMP2 complex was carefully overlaid to a plated pre-coated with the present peptide and incubated at 4° C. for 24 hrs.; (iv) termination of the reaction: 200 μl of 1M Tris solution was added and incubated for 15 min at RT to neutralize all the DSS remaining after the covalent bond formation; (v) Washing step: washing 10 times with PBS, and DMEM without FBS was added and left at 37° C. before the cells were added; (vi) preparation of C2C12 suspension and differentiation into osteoblast: 4×10$^5$ C2C12 cells were suspended in 300 μl of 2% FBS containing DMEM. DMEM in the plate pre-coated with peptide-DSS-BMP2 complex was removed and 300 μl of cell culture medium was added and incubated in 5% $CO_2$/37° C. incubator for 48 hrs to induce cell differentiation; (vii) Measurement of cell differentiation: the differentiation ability of C2C12 cells into osteoblast was examined by detecting the activity of Alkaline phosphatase by staining the cells.

Figure 7B:
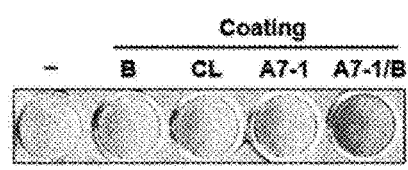
FIG. 7B is the results of the bone differentiation induced by BMPs attached to the culture plates by the present peptides, in which the expression of Alp was used a marker for bone differentiation in C2C12 and the C2C12 cells were treated with the present peptide by coating the culture plate with the present peptide. The results show that the expression of Alp is increased compared to BMP group (rhBMP2) or CL group (treated with cross-linker), which indicates that the present peptide effectively attach themselves to the culture plates and thus mediating the function of bioactive material linked thereto.
Figure 7B:

Results are shown in FIG. 7B, in which it is observed that the Alp activity is significantly increased in comparison to the groups treated with BMP (rhBMP2) and with cross-linker (CL), respectively. This indicates the differentiation was promoted by the present peptide.

Example 8. Test of the Safety of the Present Peptide

Figure 8A:
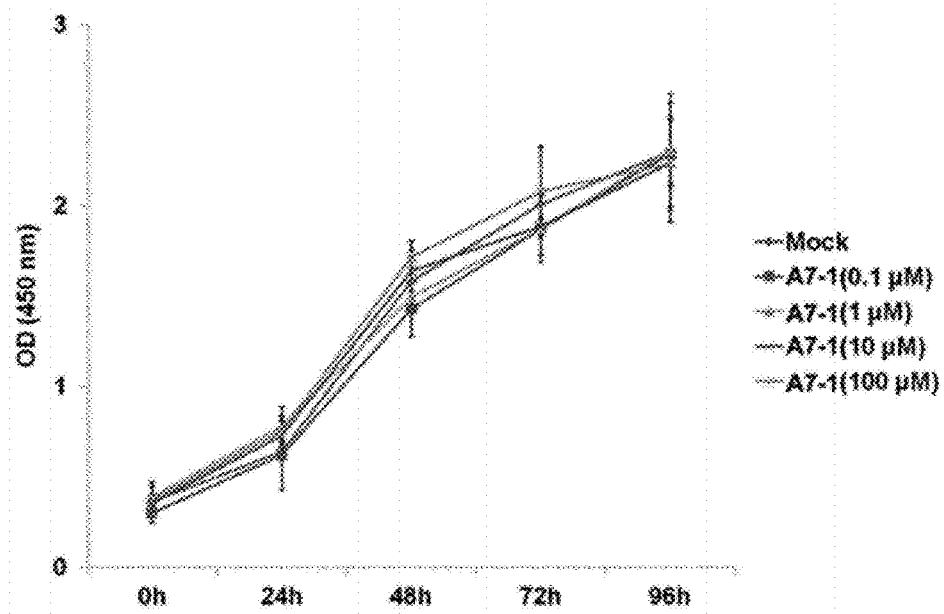
Figure 8B:
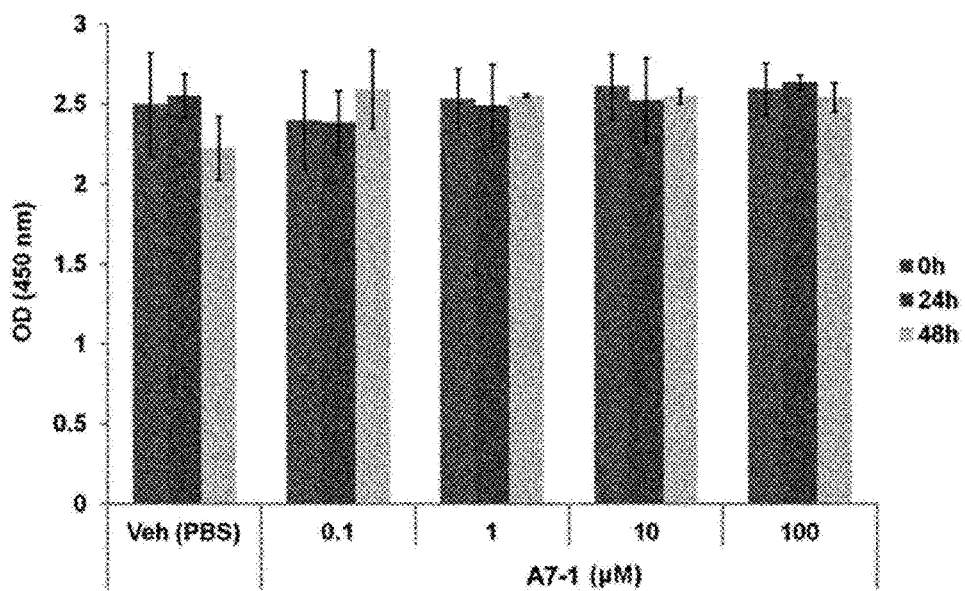

The safety of the present peptides was determined using osteoblast MC3TC-E1. Osteoblasts were treated with A7-1 peptide as prepared in Example 1 at the concentration of 0.1 μM, 1 μM, 10 μM and 100 μM. Then the effect of the present peptide on the proliferation (FIG. 8A), viability (FIG. 8B) and differentiation (FIG. 8C) on the cells was examined. For testing the effect on the proliferation, MC3T3-E1 and C2C12 cell lines were treated with BMP (rhBMP2, 10 ng/ml for 3 days) and differentiation medium for bone formation for 6 days to induce differentiation. The results were examined by cell staining. Results are shown in FIG. 8A to 8C. It is observed that the present peptide has no effect on the proliferation rate, viability rate or whether or not the cells are differentiated.

Figure 8D:
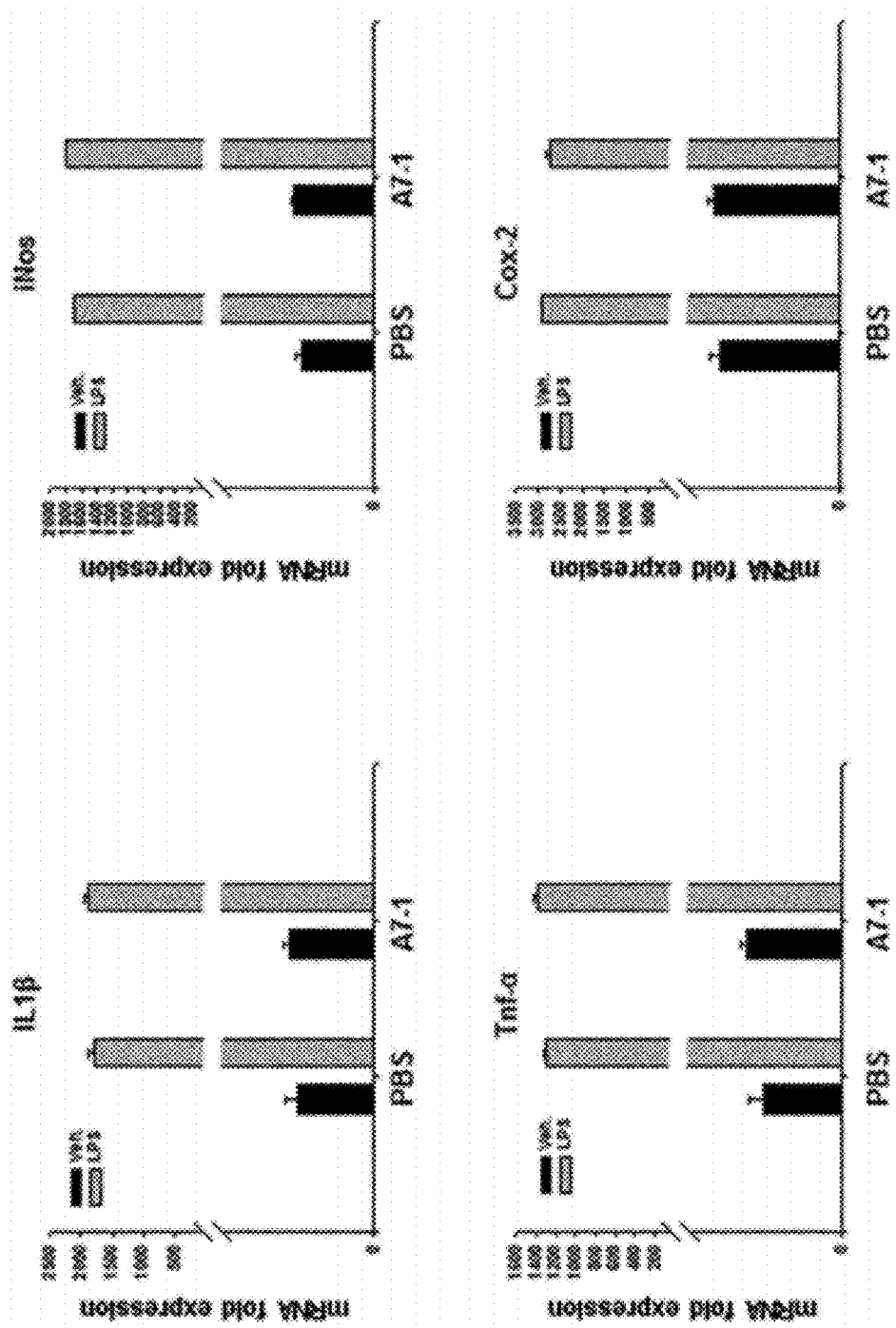
FIG. 8D is the results of testing the safety of the present peptides in monocytes isolated from mice, in which the monocytes were stimulated with the present peptides and examined for the induction of inflammation.

Also the safety of the present peptide was tested in mouse monocytes. The monocytes were isolated from bone marrow of mice and treated with the present peptide and examined for induction of inflammation. As a positive control, the cells were treated with LPS. At 24 hrs after the treatment, the cells were examined for the expression of inflammation markers IL-1β(interleukin-1β), Tnf-α (Tumor necrosis factor-α), iNos (Inducible nitric oxide synthase), Cox-2 (cyclooxygenase-2) by quantitative real time reverse transcription PCR. The results are shown in FIG. 8D. From the figure, it is observed that the present peptides do not induce inflammation in cells and thus is confirmed as a safe material to be used in vivo.

Example 9. Testing the Improvement of Adhesiveness of the Primary Nerve Cell and Culture by the Present Peptide In the present Example, the effect of the present peptide on the attachment and culture of primary nerve cell in comparison to a currently used adhesive peptide. The peptide at the concentration of 100 μM was used to coat the culture plates or to prepare nano-structure to analyze the nerve cells obtained from the brain of mouse embryo and the spinal cord of mouse by optical microscope and determination of metabolism via CCK-8. As positive controls, Laminin and poly-L-ornithin (Sigma) were used for coating according to the manufacturer's instruction. To quantify the cell attachment at each of the hour indicated, the cells unattached were removed by washing with PBS, the mixture of cell medium and CCK-8 solution (Dojindo) was added to the cells and incubated for 1 hr followed by measuring the absorbance at 450 nm.

Figure 9:
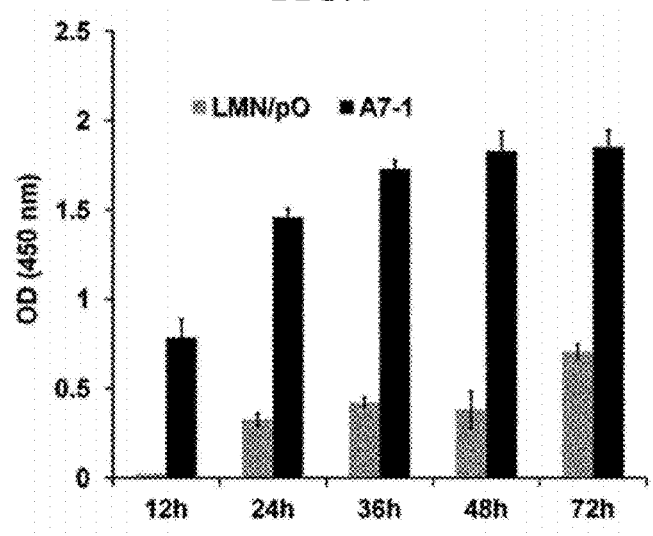
FIG. 9 is the results of comparing the adhesiveness of the present peptide with that of previously known adhesive peptides. It shows the results of comparing the adhesiveness of the present peptide with that of Laminin and Poly-L-Ornithin previously known as adhesive, in which nerve cells from a spinal cord were incubated in the culture plates coated with each of the peptides above and CCK-8 was examined at the hours indicated in the figure. The results indicate that the present peptides have superior adhesiveness compared to the other known adhesive peptides.

Results are shown in FIG. 9, in which the CCK-8 was analyzed at hours indicated in the group culture in the plate treated with laminin and poly-L-ornithin or with the present peptide, it is observed that the cells treated with the present peptide A7-1 shows the results significantly different from other groups. FIG. 9B shows the results of microscopic observation at 4 days of culture, indicating that the present peptide is the best in the adhesiveness even under the condition of the same number of cells. FIG. 9C is the results to confirm that the primary nerve cells cultured in the plate coated with the present peptide are nerve cells by using the nerve cell specific marker, GFAP, MAP2 and Nestin, which were analyzed by immunofluorescent analysis and confocal microscopy. The results indicate that the present peptide has an adhesiveness superior to the currently used ones.

Example 10. Improvement of the Attachment of Human MSC (Mesenchymal Stem Cell) to the Inorganic Surface by the Present Peptides A7-1 peptide of the present disclosure was used to coat a sterilized coverslip at the concentration of 100 μM. Then MSCs (Mesenchymal Stem cell) were cultured on the coated coverslip for 6 hrs and the adhesion progression was examined by staining the cells with fluorescent dye Rhodamine Phalloidin (Life Technology Cat. # R415) for actin fibers and DAPI (Sigma D9542) for nuclei of the cells, which were detected by confocal microscope. In this case, cells cultured on the coverslips not coated with A7-1 peptide were used as a negative control.

Figure 10A:
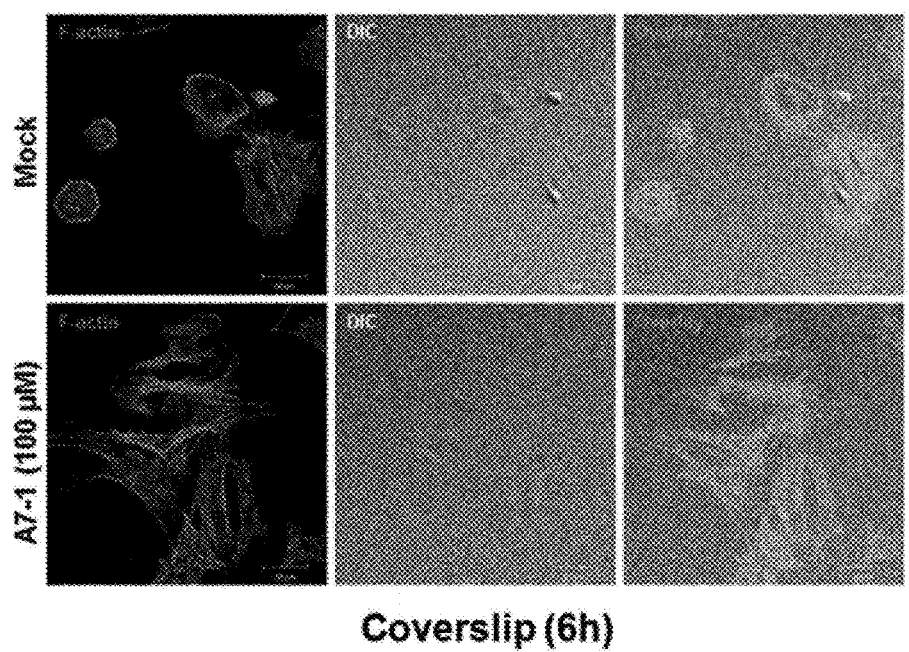
FIGS. 10A to 10C are the results showing that the adhesion progression is promoted by the present peptides, in which the cells were analyzed 6 hours after the culture.
Figure 10B:
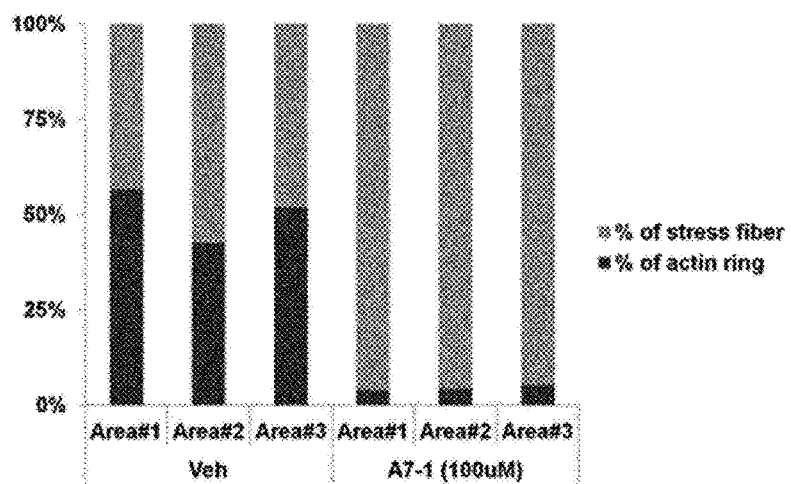
Figure 10C:
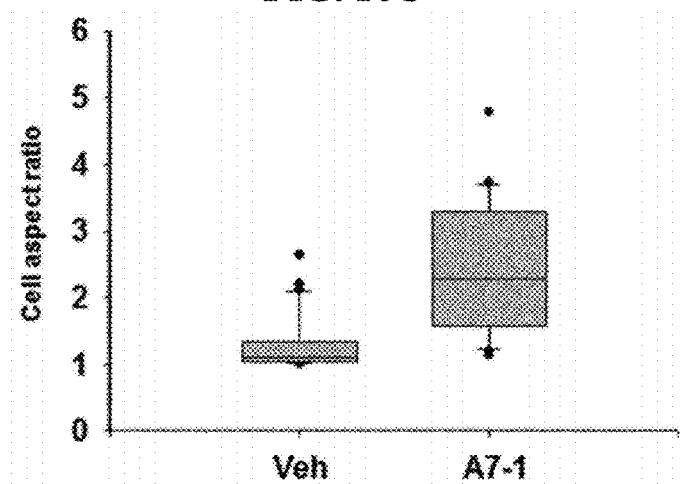

Results are shown in FIG. 10. In FIG. 10A, it is observed that the majority of negative control cells still stay in the actin-ring formation indicative of the early stage of adhesion progression. In contrast, it is observed that the majority of cells treated with A7-1 are in the stress fiber formation stage past the actin-ring stage. FIG. 10B is a graph showing the quantification result of FIG. 10A. FIG. 10C is a graph showing geometric shape of the cell as they are attaching to the coverslip (cell aspect ratio: width/height of a cell, 1 indicates a perfect round shape and the very early stage of the adhesiveness progression. Refer to: Prager-Khoutorsky et al., 2011. Nature Cell Biology 13, 1457-1465) and indicates an excellent adhesiveness of A7-1 compared to controls.

Example 11. Test of the Adhesiveness of the Present Peptides with Various Amino Acid Sequence The peptides as listed and described in Table 2 were synthesized as described in Example 1 and tested for its adhesiveness to heparin and N-Acetylglucosamine (GAG) according to the methods described in Example 5.

TABLE 2

| Name | Amino acid sequence (N → C) | SEQ ID NO | Brief description |
|---|---|---|---|
| Mock | Mock | | PBS only |
| P#1 | RQLVVK | 15 | Peptide #1 |
| P#2 | FRALPC | 6 | Peptide #2 |
| 12-mer (B) | FRALPCRQLVVK | 16 | Peptide #2 + Peptide #1 |
| 12-mer (A)-NH2 | RQLVVKFRALPC | 17 | Carboxyl group of 12-mer (A) peptide substituted with $NH_2$ |
| 2x 12-mer (A) | RQLVVKFRALPCRQLVVKFRALPC | 18 | Two consecutive 12-mer (A) peptide |
| ΔC12 | RQLVVKFRALP | 19 | Deletion of Cys at position 12 of A peptide |
| ΔP11C12 | RQLVVKFRAL | 20 | Deletion of Pro and Cys at positions 11 and 12 of A peptide |
| R1K | KQLVVKFRALPC | 21 | Substitution of Arg at position 1 of A peptide with Lys |
| ΔLVV | RQKFRALPC | 22 | LVV deletion from A peptide |
| LVV > EEE | RQEEEKFRALPC | 23 | Substitution of LVV of A peptide with EEE (charged or polar) |
| LVV > AAA | RQAAAKFRALPC | 24 | Substitution of LVV of A peptide with other hydrophobic residues |
| ΔAL | RQLVVKFRPC | 25 | AL deletion from A peptide |
| AL > EE | RQLVVKFREEPC | 26 | Substitution of AL of A peptide with EE (charged or polar) |
| AL > VV | RQLVVKFRVVPC | 27 | Substitution of AL of A peptide with other hydrophobic residues |

TABLE 2-continued

| Name | Amino acid sequence (N → C) | SEQ ID NO | Brief description |
|---|---|---|---|
| Hpho > Hphil | RQEEEKFREEPC | 28 | Substitution of Hydrophobic residues of A peptide with hydrophilic residues |
| (+) > (−) | EQLVVEFEALPC | 29 | Substitution of Positive > negative charged AA substitution |
| F7Y | RQLVVKYRALPC | 30 | Substitution of Phe at position 7 of A peptide with Tyr |
| F7W | RQLVVKWRALPC | 31 | Substitution of Phe at position 7 of A peptide with Trp. |
| Q2N | RNLVVKFRALPC | 32 | Substitution of Q of A peptide with N (nonpolar substitution) |
| Q2S | RSLVVKFRALPC | 33 | Substitution of Q of A peptide with S (Polar substitution) |
| 2x(QLVV) | R-(QLVV)2-KFRALPC | 34 | QLVV addition |
| 3x(QLVV) | R-(QLVV)3-KFRALPC | 35 | QLVV addition |
| 4x(QLVV) | R-(QLVV)4-KFRALPC | 36 | QLVV addition |
| 2x(FRALP) | RQLVVK-(FRALPC)2 | 37 | FRALPC addition |
| 2xR1 | (R)2-QLVVKFRALPC | 38 | Arg addition |
| 5xR1 | (R)5-QLVVKFRALPC | 39 | Arg addition |
| 10xR1 | (R)10-QLVVKFRALPC | 40 | Arg addition |
| 15xR1 | (R)15-QLVVKFRALPC | 41 | Arg addition |

Figure 11:
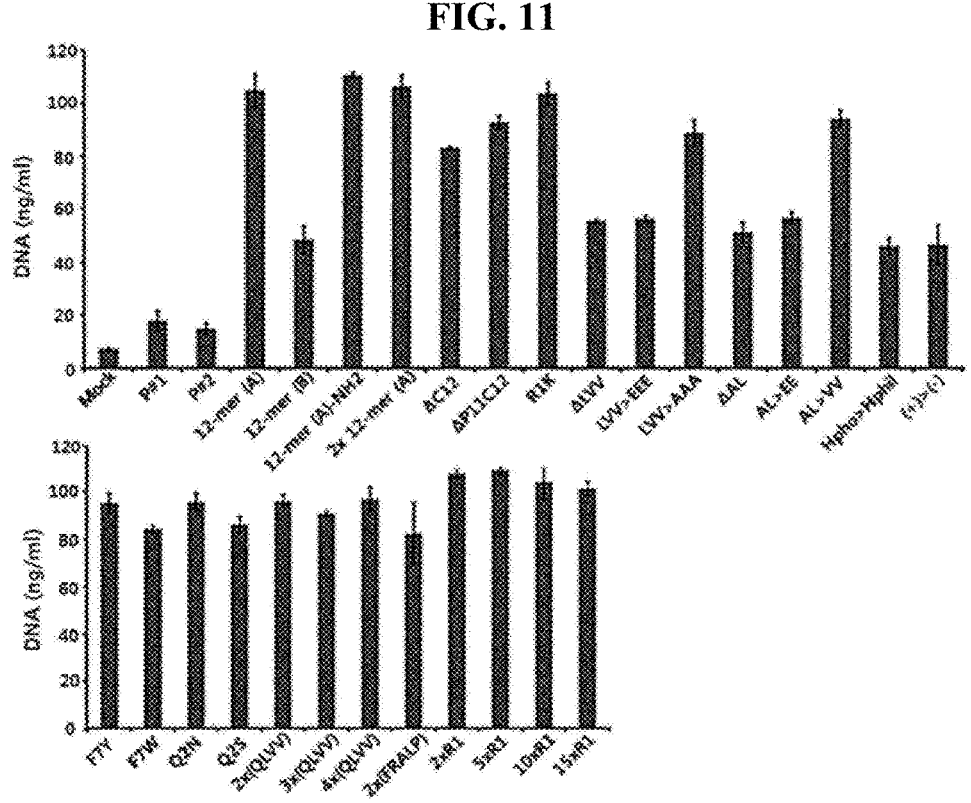
FIG. 11 is the results of testing various peptides according to the present disclosure in promoting the adhesiveness through an interaction with heparin and GAG, major components of extracellular matrix.

Results are shown in FIG. 11. From the figure, it is observed that the present peptides in various combinations of a first region (formula), a second region (formula) and a third region (formula), or the present peptides having substitutions with amino acid residues as defined in the present disclosure exhibits the adhesiveness.

Figure 12:
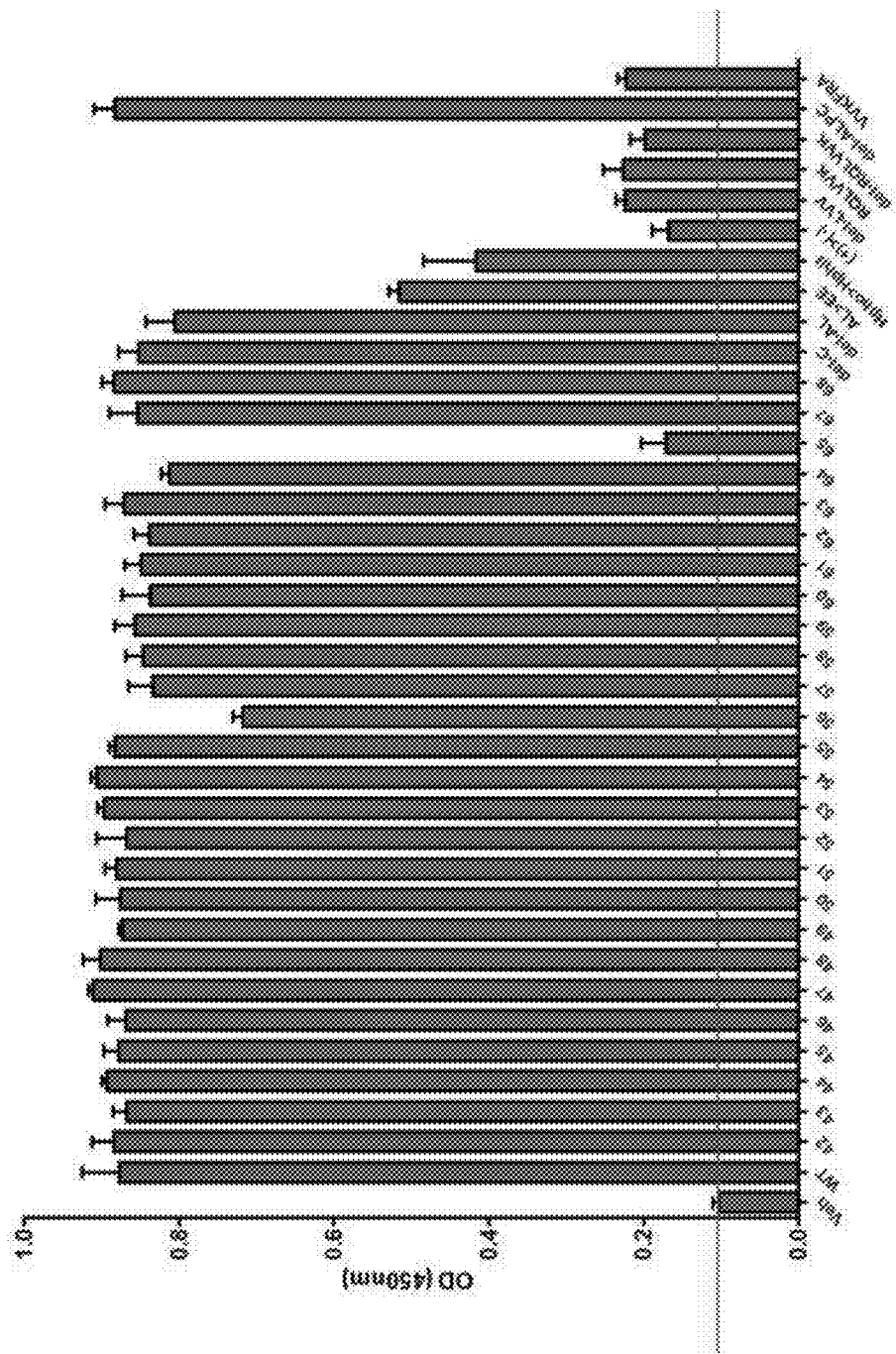
FIG. 12 is the results of testing various peptides generated based on the sequence A7-1 peptide in promoting the adhesiveness. Some of the present peptides as used in FIG. 11 were also used. The terms veh, wt and numbers on the X-axis each indicates a negative control, A7-1 peptide and sequence identification numbers, respectively.

Example 12. Test II of the Adhesiveness of the Present Peptides with Various Amino Acid Sequences The peptides having substitutions at various positions in RQLVVKFRALPC (SEQ ID NO: 17) as parent peptide were generated as listed in Table 3 and tested for the adhesiveness as in EXAMPLE 11, in which the substituted residues were determined in consideration of chemical characteristics, size and charges of the side chain of the substituted residues and/or the results of the peptide listed in Table 2 and indicated in bold letters. The results are shown in FIG. 12. All the peptides tested have been found to have adhesiveness improved in comparison to the negative control (Veh),

| | Amino acid sequence | SEQ ID NO |
|---|---|---|
| A | RQLVVKFRALPC | 17 |
| | KQLVVKFRALPC | 21 |
| | RNLVVKFRALPC | 32 |
| | RSLVVKFRALPC | 33 |

-continued

| Amino acid sequence | SEQ ID NO |
|---|---|
| RQVVVKFRALPC | 42 |
| RQIVVKFRALPC | 43 |
| RQAVVKFRALPC | 44 |
| RQEVVKFRALPC | 45 |
| RQLLVKFRALPC | 46 |
| RQLIVKFRALPC | 47 |
| RQLAVKFRALPC | 48 |
| RQLEVKFRALPC | 49 |
| RQLVLKFRALPC | 50 |
| RQLVIKFRALPC | 51 |
| RQLVAKFRALPC | 52 |
| RQLVEKFRALPC | 53 |
| RQAAAKFRALPC | 24 |
| RQEEEKFRALPC | 23 |
| RQLVVRFRALPC | 54 |
| RQLVVKYRALPC | 30 |
| RQLVVKWRALPC | 31 |

| Amino acid sequence | SEQ ID NO |
|---|---|
| RQLVVKFKALPC | 55 |
| RQLVVEFEALPC | 56 |
| RQLVVKFRLLPC | 57 |
| RQLVVKFRILPC | 58 |
| RQLVVKFRVLPC | 59 |
| RQLVVKFRELPC | 60 |
| RQLVVKFRAAPC | 61 |
| RQLVVKFRAIPC | 62 |
| RQLVVKFRAVPC | 63 |
| RQLVVKFRAEPC | 64 |
| RQLVVKFRVVPC | 27 |
| RQLVVKFREEPC | 26 |
| RQEEEKFREEPC | 28 |

| Amino acid sequence | SEQ ID NO |
|---|---|
| RQEEEEFEEEPC | 65 |
| RQLVVKFRALXC | 66 |
| RQLVVKFRALPS | 67 |
| RQLVVKFRALPT | 68 |
| RQLVVKFRALPX | 69 |

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention. The contents of all publications disclosed as references herein are incorporated herein by reference.

---

What is claimed is:

1. A method of attaching at least two materials to each other comprising the steps of:
   applying to all or part of the at least two materials a composition comprising an isolated polypeptide:
   (i) consisting of the amino acid sequence as set forth in SEQ ID NO: 15-22, 24-27, 29-37, 42-64, 67 or 68,
   (ii) consisting of the amino acid sequence as set forth in SEQ ID NO: 15-20, 22, 24-27, 30-37, 42-64, 67 or 68, and 1 to 14 arginine residues at the N- and/or C-terminus of the amino acid sequence,
   (iii) consisting of the amino acid sequence as set forth in SEQ ID NO: 15-22, 24-27, 29-37, 42-64, 67 or 68 with the N- and/or C-terminus of the sequence being substituted with an inert group,
   (iv) consisting of the amino acid sequence as set forth in SEQ ID NO: 29 and 1 to 14 glutamic acid residues at the N- and/or C-terminus of the amino acid sequence, or
   (v) consisting of the amino acid sequence as set forth in SEQ ID NO: 21 and 1 to 14 lysine residues at the N- and/or C-terminus of the amino acid sequence; and
   contacting the at least two materials to each other in a condition suitable for the attachment.

2. The method of claim 1, wherein at least one material of the at least two materials is an inorganic surface.

3. The method of claim 2, wherein the inorganic surface is the surface of a metal, a ceramic, a calcium apatite crystal, or a polymer synthetic resin.

4. The method of claim 3, wherein at least one material attached to the inorganic surface is a biological or a non-biological material.

5. The method of claim 4, wherein the non-biological material is a metal, a glass, a plastic, or a polymer synthetic resin, and the biological material is a cell, a tissue, a protein, a lipid, a sugar or a nucleic acid, or a combination thereof.

* * * * *